United States Patent [19]

Marotta et al.

[11] Patent Number: 5,547,841

[45] Date of Patent: Aug. 20, 1996

[54] IN VITRO METHOD FOR SCREENING FOR DRUGS THAT INHIBIT PRODUCTION OR DEGRADATION OF HUMAN A4-AMYLOID

[75] Inventors: Charles A. Marotta, Cambridge, Mass.; Sayeeda Zain, Pittsford, N.Y.

[73] Assignees: The McLean Hospital Corporation, Belmont, Mass.; University of Rochester, Rochester, N.Y.

[21] Appl. No.: 990,893

[22] Filed: Dec. 15, 1992

Related U.S. Application Data

[62] Division of Ser. No. 618,529, Nov. 26, 1990, abandoned, which is a continuation of Ser. No. 143,424, Jan. 13, 1988, abandoned, which is a continuation-in-part of Ser. No. 105,752, Oct. 8, 1987, abandoned.

[51] Int. Cl.$^6$ ............................. C12Q 1/68; G01N 33/53; G01N 33/543
[52] U.S. Cl. ............................. 435/6; 435/7.1; 435/7.92; 436/518; 436/811
[58] Field of Search ............................. 435/4, 6, 91.1, 435/91.32, 240.2, 317.1; 536/23.5

[56] References Cited

U.S. PATENT DOCUMENTS

| | | | |
|---|---|---|---|
| 4,579,821 | 4/1986 | Palmiter et al. | 435/172.3 |
| 4,666,829 | 5/1987 | Glenner et al. | 435/6 |
| 4,728,605 | 3/1988 | Fudenberg et al. | 435/29 |
| 4,912,206 | 3/1990 | Goldgaber et al. | 536/27 |
| 5,221,607 | 6/1993 | Cordell et al. | 435/6 |

FOREIGN PATENT DOCUMENTS

WO88/03951  6/1988  WIPO.

OTHER PUBLICATIONS

Beltz et al., Isolation of Multigene Families and Determination of Homologies by Filter Hybridization Methods, *Methods in Enzymology* 100:266–285 (1983).

Benes et al., Structural Diversity and Infrastructure of Amyloid Deposits in Alzheimer Brain, *Soc. Neurosci.* 13:1153 Abstract No. 316.15 (1987).

At last, animal models for studying Alzheimer's: A tale of four mice, *Biotechnology Newswatch* 11(15):1 and 4 (1991).

Cullen et al., Use of Eukaryotic Expression Technology in the Functional Analysis of Cloned Genes, *Methods in Enzymology* 152:684–702 (1987).

Fabrice et al., A new TaqI polymorphism deteced by the cDNA encoding amyloid beta protein of Alzheimer's Disease, *Chemical Abstracts* 108:154 Abstract No. 17130p (1988).

Gamzu, E., Animal Behavioral Models in the Discovery of Compounds To Treat Memory Dysfunction, *Ann. N.Y. Acad. Sci.* 444:370–393 (1985).

Glenner et al., Alzheimer's Disease: Initial Report of the Purification and Characterization of a Novel Cerebrovascular Amyloid Protein, *Biochem. and Biophys. Res. Comm.* 120(3):885–390 (1984).

Glenner et al., Alzheimer's Disease and Down's Syndrome: Sharing of a Unique Cerebrovascular Amyloid Fibril Protein, *Biochem. Biophys. Res. Comm.* 122(3):1131–1135 (1984).

Goedert, M., Neuronal Localization of amyloid beta protein precursor mRNA in normal human brain and in Alzheimer's disease, *The EMBO Journal* 6(12):3627–3632 (1987).

Goldgaber et al., Isolation, characterization, and chromosomal localization of a human brain cDNA clone for the amyloid β–protein found in Alzheimer's . . . , *Chem. Abstr.* 109:182 No. 164609a (1988).

Kang et al., The precursor of Alzheimer's disease amyloid A4 protein resembles a cell–surface receptor, *Nature* 325:733–736 (1987).

Kawabata et al., Amyloid plaques, neurofibrillary tangles and neuronal loss in brains of transgenic mice overexpressing a C–terminal fragment of human amyloid precursor protein, *nature* 354:476–478 (1991).

Lawabata et al., Alzheimer's retraction, *Nature* 356:23 (1992).

Lal et al., Cognitive Disorders Related to Immune Dysfunction: Novel Animal Models of Drug Development, *Drug Development Research* 7:195–208 (1986).

Marotta et al., In Vitro Synthesis of Human Brain Proteins Including Tubulin and Actin by Purified Postmortem Polysomes, *Journal of Neurochemistry* 36(3):966–975 (1981).

Marotta et al., Transcriptional and translational regulatory mechanisms during normal aging of the Mammalian brain and in Alzheimer's disease, Prog. Brain Res. 70:303–320 (1986).

Marx, J., Major setboack for Alzheimer's Models, *Science* 255:1200–1202 (1992).

Master's et al., Amyloid plaque core protein in Alzheimer;s disease and Down syndrome, *Proc. Natl. Acad. Sci. USA* 82:4245–4249 (1985).

Palmiter et al., Dramatic growth of mice that develop from eggs microinjected with metallothioneingrowth hormone fusion genes, *Nature* 300:611–615 (1982).

Robakis et al., Isolation of a cDNA clone encoding the Alzheimer's disease and Down'syndrome amyloid peptide, *Chemical Abstracts* 109(15):106, Abstract No. 123443y (1988).

Robakis et al., Molecular cloning and characterization of a cDNA encoding the cerebrovascular and the neuritic plaque amyloid peptides, *Proc. Natl. Acad. Sci. USA* 84:4190–4194 (1987).

St. George–Hyslop et al., The Genetic Defect Causing Familial Alzheimer's Disease Maps on Chromosome 21, *Science* 235:885–890 (1987).

Sasaki et al., A HindIII polymorphism detected by the cDNA encoding amyloid beta protein of Alzheimer's disease, *Chemical Abstracts* 107(13):103, Abstr. No. 110352b (1987).

Selkoe, D. J., In the beginning . . . , *Nature* 354:432–433 (1991).

Stout et al., Expression of human HPRT in the central nervous system of transgenic mice, *Nature* 317:250–252 (1985).

Suggs et al., Use of synthetic oligonucleotides as hybridization probes: Isolation of cloned cDNA sequences for human $\beta_2$–microglobulin, *Proc. Natl. Acad. Sci. USA* 78(11):6613–6617 (1981).

Tanzi et al., The genetic defect in familial Alzheimer's disease is not tightly linked to the amyloid β–protein gene, *Nature* 329:156–157 (1987).

Tanzi et al., Amyloid β Protein Gene: cDNA, mRNA Distribution, and Genetic Linkage Near the Alzheimer's Locus, *Science* 235:880–884 (1987).

Van Broeckhoven et al., Failure of familial Alzheimer's disease to segregate with the A4–amyloid gene in several European families, *Nature* 329:153–155 (1987).

Zain et al., Molecular Cloning of cDNA Transcribed From Messenger RNA of the Alzheimer Brain. Identification of cDNA For Amyloid and Glial Fibrillary . . . , *Soc. Neurosci.* 13:558, Abstr. 154.5 (1987).

Zain et al., Molecular Cloning and In Vitro Translation Studies of GFAP: mRNA From Normal and Alzheimer Disease Brain Tissue, *J. Cell. Biochem.* 11D (Supp.):198, Abstr. S415 (1987).

Zain et al., Molecular cloning of amyloid cDNA derived from cRNA of the Alzheimer disease brain: Coding and noncoding regions of the fetal precursor . . . , *Proc. Natl. Acad. Sci. USA* 85:929–933 (1988).

Aberts, B. et al 1983. Molecular Biology of the Cell, Garland Publishing Inc., N.Y., N.Y. pp. 241–242.

J. Brandis et al., "Preparation of cDNA Libraries and the Detection of Specific Gene Sequences," Setlow et al., Eds., *Genetic Engineering* 8:299–316, Plenum Press, New York (1986).

Glenner, G. G. 1988 *Cell* vol. 52 pp. 307–308.

Vinters, H. V., moderator. "Brain amyloid and Alzheimer disease" Ann. Intern. Med. 1988; vol. 109, pp. 41–54, 439.

*Primary Examiner*—Toni R. Scheiner
*Assistant Examiner*—Patricia A. Duffy
*Attorney, Agent, or Firm*—Sterne, Kessler, Goldstein & Fox P.L.L.C.

[57] ABSTRACT

The invention relates to an in vitro method of screening for drugs, potentially useful for treatment of Alzheimer's Disease. The method involves contacting a drug with a host transformed with a DNA construct which contains at least the DNA coding for human A4-amyloid peptide and overexpresses the peptide and then detecting the prevention of production or increased degradation of the A4-peptide due to the drug.

3 Claims, 11 Drawing Sheets

```
                                                    G CAC ACC CTA AAG CAT TTC GAG CAT GTG 1320
                                                      His Thr Leu Lys His Phe Glu His Val (441) CGC ATG GTG GAT CCC AAG AAA GCC GCT CAG ATC CGG TCC CAG GTT ATG ACA CAC CTC CGT 1380
      Arg Met Val Asp Pro Lys Lys Ala Ala Gln Ile Arg Ser Gln Val Met Thr His Leu Arg (461) GTG ATT TAT GAG CGC ATG AAT CAG TCT CTC TCC CTG CTC TAC AAC GTG CCT GCA GTG GCC 1440
      Val Ile Tyr Glu Arg Met Asn Gln Ser Leu Ser Leu Leu Tyr Asn Val Pro Ala Val Ala (481) GAG GAG ATT CAG GAT GAA GTT GAT GAG CTT CAG CTG CTG AAA GAG CAA AAT TAT TCA GAT GAC 1500
      Glu Glu Ile Gln Asp Glu Val Asp Glu Leu Gln Leu Leu Lys Glu Gln Asn Tyr Ser Asp Asp (501) GTC TTG GCC AAC ATG ATT AGT GAA CCA AGG ATC AGT GAG CTC CTT CCC GTG AAT GGA 1560
      Val Leu Ala Asn Met Ile Ser Glu Pro Arg Ile Ser Glu Leu Leu Pro Val Asn Gly (521) TCT TTG ACC GAA ACG AAA ACC GTG ACC ACC GTG GAG CTC CTT CCC GTG AAT GGA GAG TTC AGC CTG 1620
      Ser Leu Thr Glu Thr Lys Thr Val Thr Thr Val Glu Leu Leu Pro Val Asn Gly Glu Phe Ser Leu (541) GAC GAT CTC CAG CCG TGG CAT TCT TTT GGG GCT GAC TCT GAC TCT GAC GCT GAC TCT GAC GCC AAC ACA GAA AAC 1680
      Asp Asp Leu Gln Pro Trp His Ser Phe Gly Ala Asp Ser Val Pro Ala Asn Thr Glu Asn (561) GAA GTT GAG CCT GTT GAT GCC CGC CCT GCT GCC GAC CGA GGA CTG ACC ACT CGA CCA GGT 1740
      Glu Val Glu Pro Val Asp Ala Arg Pro Ala Ala Asp Arg Gly Leu Thr Thr Arg Pro Ser (581) TCT GGG TTG ACA AAT ATC AAG ACG GAG ATC TCT GAA GTG AAG ATG GAT GCA GAA TTC 1800
      Ser Gly Leu Thr Asn Ile Lys Thr Glu Ile Ser Glu Val Lys Met Asp Ala Glu Phe
```

FIG. 3A

```
(601) CGA CAT GAC TCA GGA TAT GAA GTT CAT CAT CAA AAA TTG GTG TTC TTT GCA GAA GAT GTG 1860
      Arg His Asp Ser Gly Tyr Glu Val His His Gln Lys Leu Val Phe Phe Ala Glu Asp Val (621) GGT TCA AAC AAA GGT GCA ATC ATT GGA CTC ATG GTG GGC GGT GTT GTC ATA GCG ACA GTG 1920
      Gly Ser Asn Lys Gly Ala Ile Ile Gly Leu Met Val Gly Gly Val Val Ile Ala Thr Val (641) ATC GTC ATC ACC TTG GTG ATG CTG AAG AAA CAG TAC ACA TCC ATT CAT CAT GGT GTG 1980
      Ile Val Ile Thr Leu Val Met Leu Lys Lys Gln Tyr Thr Ser Ile His His Gly Val (661) GTG GAG GTT GAC GCC GCT GTC ACC CCA GAG CGC CAC CTG TCC AAG ATG CAG CAG AAC 2040
      Val Glu Val Asp Ala Ala Val Thr Pro Glu Arg His Leu Ser Lys Met Gln Gln Asn (681) GGC TAC GAA AAT CCA ACC TAC AAG TTC TTT GAG CAG ATG CAG AAC TAGACCCCCGCCACAGCA 2100
      Gly Tyr Glu Asn Pro Thr Tyr Lys Phe Phe Glu Gln Met Gln Asn *

GCCTCTGAAGTTGGACAGCAAAACCATTGCTTCACTACCCATCGGTCTCCATTTATAGAATAATGTGGAAGAAACAA
ACCCGTTTTATGATTACTCATTATCGCCTTTTGACAGTGCTGTAACACAAGTAGATGCCTGAACTTGAATTAAT
CCACACATCAGTAGTCTATCATTTGGTCTCTACATTTACATTTGGTCTCTATACTACATTATTAATGGTTTGTACTGT
AAGAATTTAGCTGTATCAAACTAGTGCATGAATAGATTCCTCCTGATTATTTATCACATAGCCCCTTAGCCAGTTG
TATATTATTCTTGTGTTTGTGACCCAATTAAGTCCTAAGTATGCTTAAGAATCGATGGGGATGCTTCATG
TGAACGTGGAGTTCAGCTGCTTTAGAGATGCTTTTTTCCTAAGTATTCCTTTCCTGATCATGCATTTTAAAGTTAAACATTT
TAAGTATTTCAGATGCTTTAGAGAATTAGAGGATACACACGTTGTTTCTTGCTGTCCTTGTGCACACATTAGGCATTGAGACT
TGTGATATAGGAATTAAGAGGATACACACGTTGTTTCTTGCTGTCTTTTATGTGCACACATTAGGCATTGAGACT
TCAAGCTTTTTCTTTTTTTGTCCACGTATCTTTGGTCTCTTTGATAAAGAATCCCTGTTCATTGTAAGCACTTTT
ACGGGGGGCGGTGGGAGGGTGCTCGTCGCTCTTCAAGAATTC
```

IN VITRO METHOD FOR SCREENING FOR DRUGS THAT INHIBIT PRODUCTION OR DEGRADATION OF HUMAN A4-AMYLOID

This application is a divisional of application Ser. No. 07/618,529, filed Nov. 26, 1990 now abandoned, which is a continuation of application Ser. No. 07/143,424, filed Jan. 13, 1988, now abandoned, which is a continuation-in-part of application Ser. No. 07/105,752, filed Oct. 8, 1987, now abandoned, to which the right of priority under 35 U.S.C. § 120 is hereby claimed.

BACKGROUND OF THE INVENTION

The present invention was made with government support. Accordingly, the government has certain rights in the invention.

1. Field of the Invention

The present invention relates to recombinant DNA technology and to products and processes involved in the cloning preparation, expression, and use of genes for amyloid derived from the brain of Alzheimer's Disease patients.

2. Description of the Background Art

Senile plaques found in abundance in the Alzheimer's Disease (AD) brain represent a hallmark feature of this disorder and have been correlated with the degree of intellectual impairment (2, 3). The plaques are composed of extracellular amyloid, reactive cells, and degenerating neurites (1). The proteinaceous amyloid is also associated with the cerebral vasculature of the AD brain (6). Amyloid is composed of fibrils of 4–8 nm diameter that form the core of the plaques (4).

Protein chemistry studies have provided limited information on amyloid fibrillary material. Glenner and Wong (6) purified amyloid from meningeal vessels of an AD brain; a 4.2 kd polypeptide, known as β-amyloid, was isolated and shown to have a unique amino acid sequence. A polypeptide of similar sequence was subsequently isolated from the cerebrovascular amyloid of a Down's syndrome brain (7); a single amino acid substitution, of glutamic acid for glutamine at position 11, distinguished the two polypeptides. Similar results were independently obtained, by Masters et al. (8) who partly purified and analyzed amyloid plaque cores from the AD cerebral cortex; the amino acid sequence of the Glu variant was obtained and is referred to as A4 amyloid.

The β-polypeptide, derived from purified β-amyloid, is disclosed in Glenner et al., U.S. Pat. No. 4,666,829, filed May 15, 1985. This patent also discloses antibodies made to the first 10 amino acids of the β-polypeptide.

The amyloid gene product merits intense scrutiny since it is a major neuropathologic manifestation of AD. At present, no direct information is available on mechanisms that regulate amyloid metabolism and which are responsible for the increased deposition of amyloid in the AD brain. The gene has been localized to chromosome 21, as has the gene for familial AD (10, 11). Therefore, complex interactions involving chromosome 21 gene products (31), the processing of transcripts or of the protein precursor, an unusual precursor structure, and/or interaction with the environment may contribute to the unusually high content of amyloid in the AD brain (30).

SUMMARY OF THE INVENTION

In order to begin to distinguish among these possibilities, it is of interest to determine whether or not the genetic transcript for amyloid that is expressed specifically in the AD brain is the same as in non-demented cases. For example, nucleotide sequence variations occurring at certain sites may affect mRNA activity or stability; or, more than one form of amyloid protein may be synthesized. Alternatively, if the predominant type of amyloid mRNA derived from the AD brain is the same as from non-Alzheimer sources, then in order to explain the overabundance of amyloid typically present in the AD brain, attention would have to be focused upon elucidating the fine details of genetic control mechanisms affecting transcription levels or the regulation of amyloid protein turnover at the cellular level.

cDNA libraries from AD brain mRNA were prepared and the amyloid precursor cDNA identified. Coding and 3'-noncoding regions of cDNA sequences that surround and include the known A4-amyloid polypeptide structure are disclosed. The cloned amyloid insert is also used to compare AD and control mRNAs on Northern blots and the results are contrasted with those obtained with a glial-specific mRNA.

The invention is also drawn to recombinant molecules containing the AD-amyloid gene, such as plasmids; to hosts transformed therewith; to methods of production of AD-amyloid; to diagnosis of AD; and to genetic models for AD, such as transfected cell lines and transgenic mice.

The most serious obstacle to elucidating the molecular mechanisms involved in amyloid synthesis and deposition in the AD brain has been the unavailability of convincing cellular or animal models for this uniquely human disorder. Therefore, we have applied our cloned amyloid inserts, along with newly developed tumor virus vectors, derived from SV40 and the JC virus, to prepare and analyze transfected cells and transgenic mice to establish models for amyloid overexpression that may be relevant to the amyloid accumulation of the AD brain. The models are not only intended to provide an experimental medium that may elucidate aspects of the molecular pathogenesis of AD, but also to serve as tools for screening drugs that may have potential application as therapeutic agents to prevent or limit amyloid accumulation in AD and in the normal aging human brain. At present, there are no reported examples of transfected cells or transgenic mice carrying an overabundance of the AD amyloid gene.

The transfected cells and transgenic mice of the invention are designed to produce a cellular model for the overproduction of amyloid. The cells, which include neuronal, glial and other types, can be characterized with anti-amyloid monoclonal antibodies (mabs) as described in copending U.S. patent application Ser. No. 105,751, filed Oct. 8, 1987, incorporated by reference herein in its entirety. Other characterization methods include in situ hybridization, molecular and cellular procedures, and light and electron microscopic methods.

The transfected cells and transgenic mice of the invention are useful for determining the extent to which the A4 or other amyloid precursor domains accumulate, and possibly precipitate, either intracellularly or extracellularly.

The effects of excessive amyloid synthesis on cell survival may also be examined. For example, the transfected cell lines may be extensively examined at the levels of transcription, translation and RNA metabolism. The cells may be subjected to biological agents that affect the intracellular turnover of amyloid. The extent to which transfected cells resemble or differ from amyloid producing cells of the AD brain may be assessed. This may be done by assessing amyloid production in the AD brain by immunologic and in situ hybridization methods (30, 34, 49).

Thus, development of a successful cellular model for amyloid overproduction makes possible experimental manipulations aimed at preventing amyloid synthesis and/or promoting its degradation.

As with transfected cells, the mouse model provides a new and invaluable medium with which to explore the molecular-pathogenesis of amyloidosis relevant to AD and to serve as an animal assay system to screen potentially therapeutic agents. The latter include drugs that prevent or limit the overproduction of amyloid in the mammalian brain, or which increase the degradation of amyloid.

It is to be emphasized that the preparation of cell or animal models that overexpress the amyloid precursor are intended as experimental tools to gain insight into the synthesis and metabolism of amyloid that may have relevance to the overaccumulation of amyloid in the AD brain. These models do not depend for their significance on whether or not the amyloid gene is or is not duplicated in AD. The transfected cells and transgenetic mice of the invention are not intended to test various hypotheses, but rather, to serve as biological models that allows evaluation and modifications of amyloid overproduction in defined cells and neural tissues.

By means of transfected cells and transgenic mice, a means to determine whether or not overproduction of amyloid intracellularly is sufficient to cause deposition at intracellular or extracellular sites is provided. In addition, a means to determine the consequences of this process for normal cellular metabolism is also provided.

DESCRIPTION OF THE FIGURES

FIGS. 3A-3B show the sequence of amy37 cDNA. Shown is the nucleotide structure with the corresponding amino acids. The nucleotide positions are indicated at the right and the amino acid positions are shown in parentheses at the left; the numbering scheme was suggested in reference 9. The A4 amyloid protein sequence (9) is underlined. An asterisk indicates the termination codon and is followed by the 3'-non-coding sequence.

Lane A contains size markers (in kb). Lanes B-H contain poly(A+) RNA from the following cases identified in terms of diagnosis (A for Alzheimer and C for control), age and postmortem interval: (B) A77, 10 hr; (C) C73, 13 hr; (D) A67, 2.5 hr; (E) C57, 13 hr.; (F) A65, 3.75 hr; (G) C73X, 10.5 hr; (H) C91, 18 hr.

Figure 5:
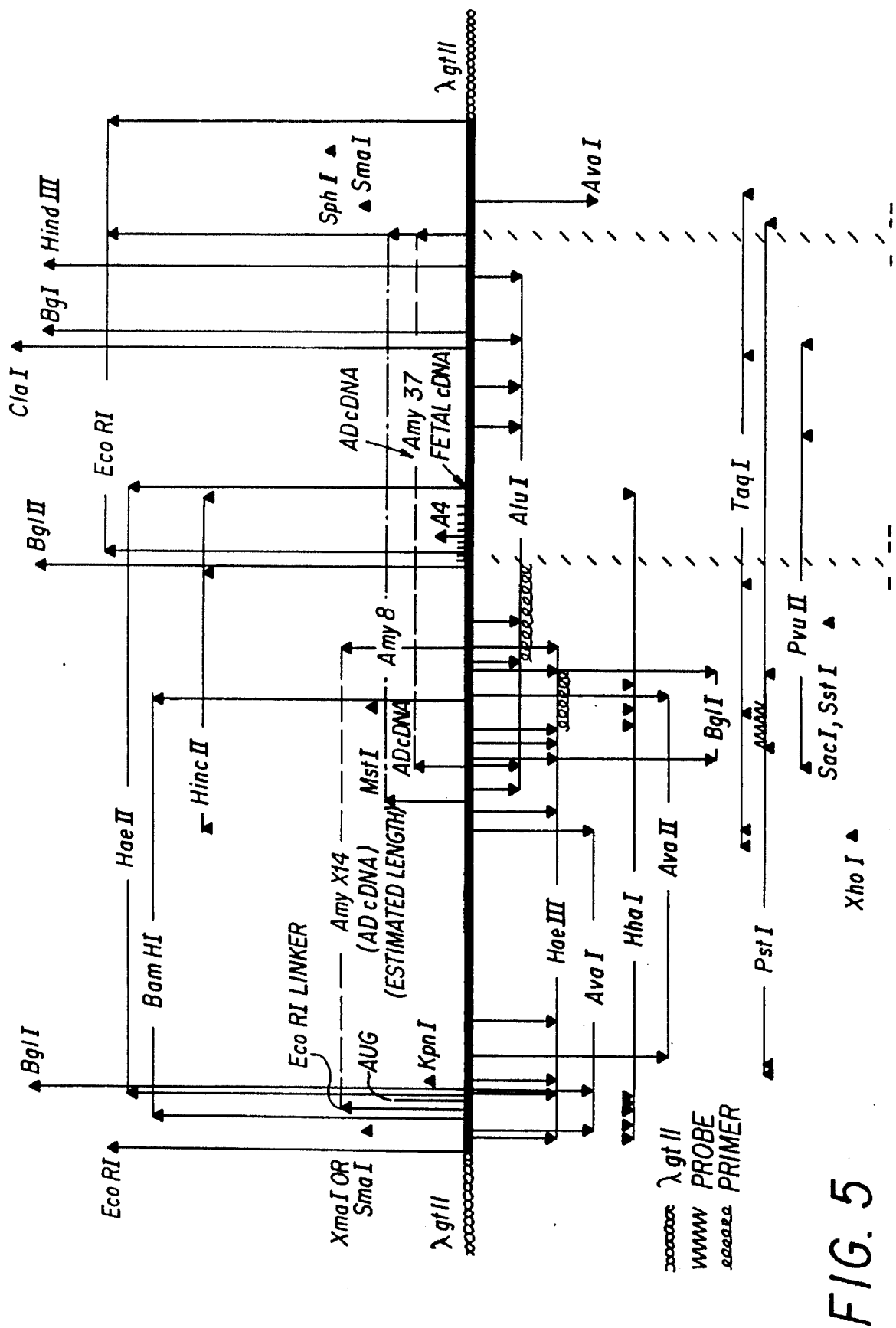

FIG. 5 shows an endonuclease restriction map of brain amyloid cDNA.

Figure 6C:
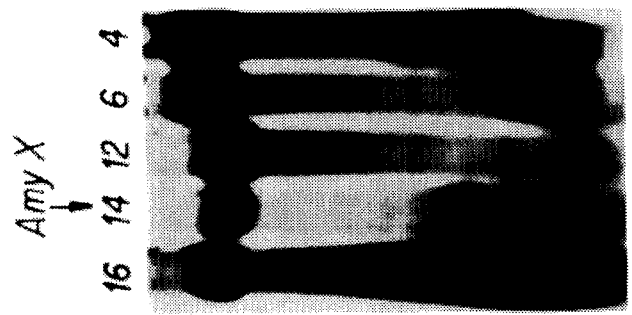
Figure 6B:
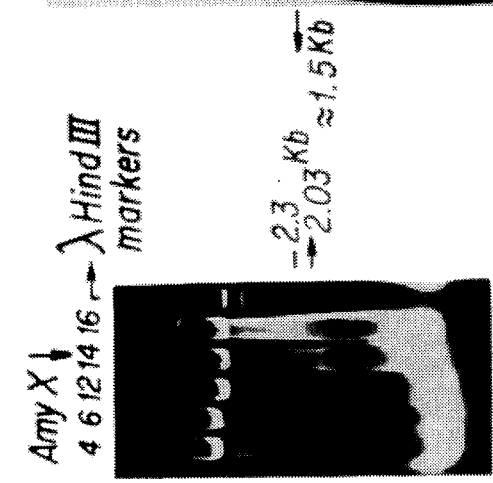
Figure 6A:
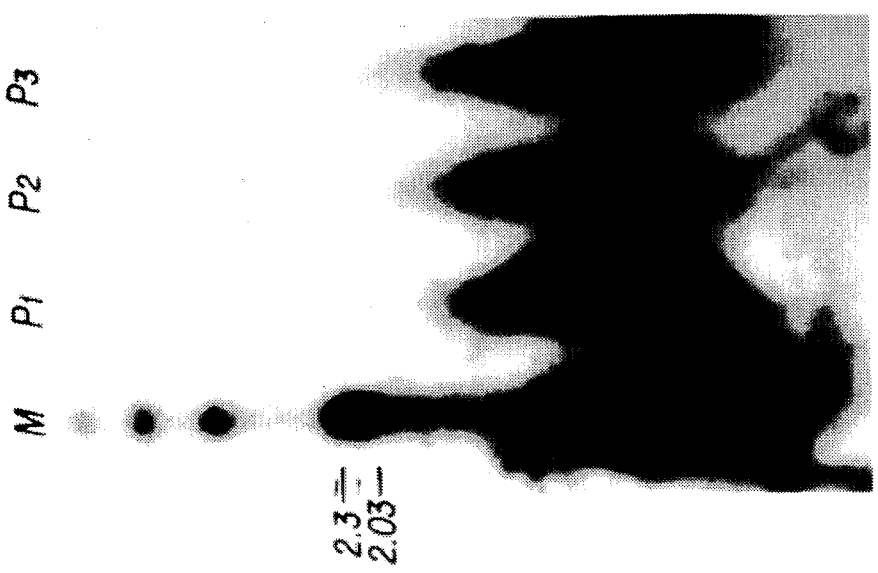

FIGS. 6A–6C show the construction and screening of an AD amyloid-specific cDNA library from alzheimer brain A77 mRNA to isolate the 5' end of mRNA.

(FIG. 6A) Autoradiograph of synthesized cDNA. Synthesis was carried out using primer P1, P2 and P3, described in the text, using A77 mRNA as the template. The resulting transcripts were sized on a 1.4% agarose gel. The figure shows the autoradiographic patterns of the synthesized products in order to demonstrate the size of the transcripts. The latter were estimated to be at least 1.5 kb in length. The first lane (M) contains size markers.

(FIG. 6B) Ethidium bromide stained gel of various inserts from recombinant phage after digestion with Eco-RI. Minilysates were prepared from recombinant phage that had been selected with the EcoRI-Pst I probe (nucleotides 1293–1434) described in the text. On the stained gel, the insert sizes were obscured by the low molecular weight RNAs that masked them. Therefore, the Southern blot shown in panel C was utilized for this purpose.

(FIG. 6C) Autoradiograph of Southern hybridization analysis. The DNA resolved on the gel of panel B was transferred to a nitrocellulose membrane and subjected to Southern blot analysis using an amy-37 insert (the previously described EcoRI-Eco RI fragment of approximately 500 b.p. spanning nucleotides 1293–1975) that was prepared after transcription from a PGEM clone to obtain a riboprobe labeled with alpha ($^{32}$P)UTP. The second lane contains the amy-x14 insert that was estimated to be approximately 1.1 to 1.5 kb.

Figure 7A:
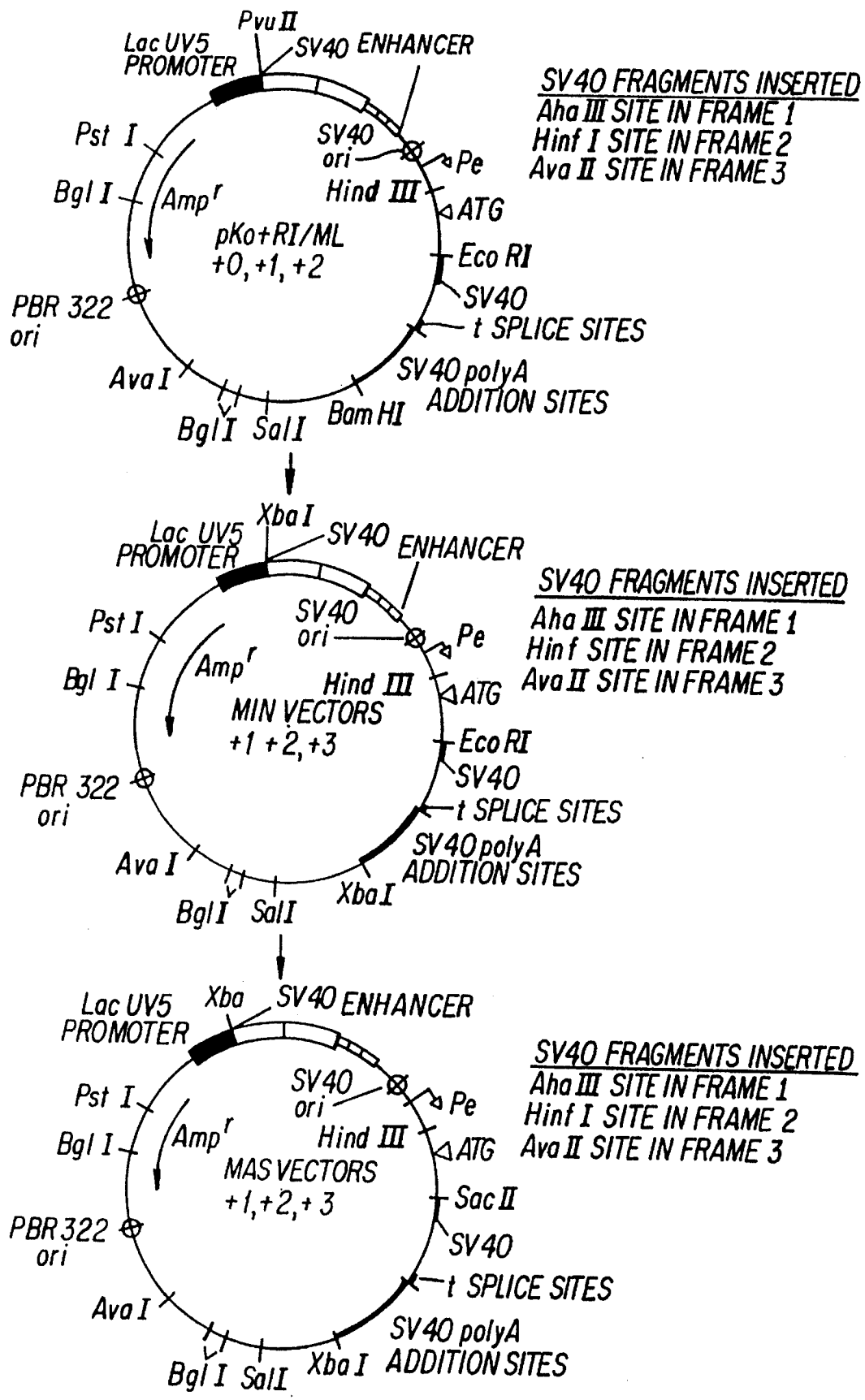
Figure 7B:
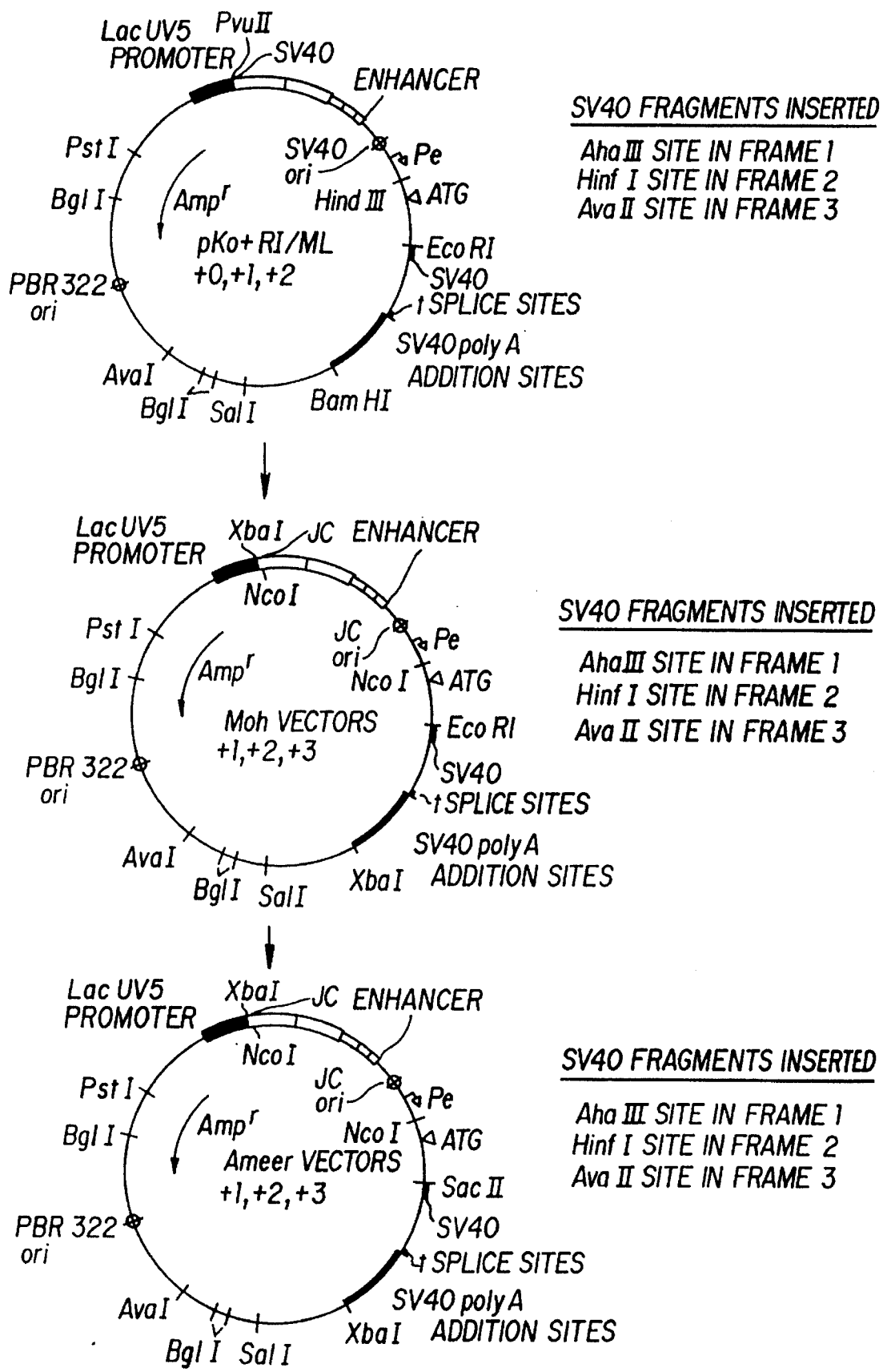

FIGS. 7A and 7B depict the schemes used for generating various expression vectors for transfecting cells and for transgenic mouse experiments. The unique Eco RI sites in Min (2A) and Moh (2B) vectors are used to insert the Eco RI fragments of the A4 (β-amyloid) cDNA from the A4 peptide coding domain, the precursor domain, and the C-terminal end domain. The unique Eco RI site is converted to a Sac II site; the resulting vehicle is used to clone the complete cDNA with heterologous SV40 (Mas vectors, 2A) or JC (Ameer vectors, 2B) viral control regions. The Mas vectors are used for the same purpose. All the described vectors are used to prepare transfected cells and transgenic mice.

Figure 8:
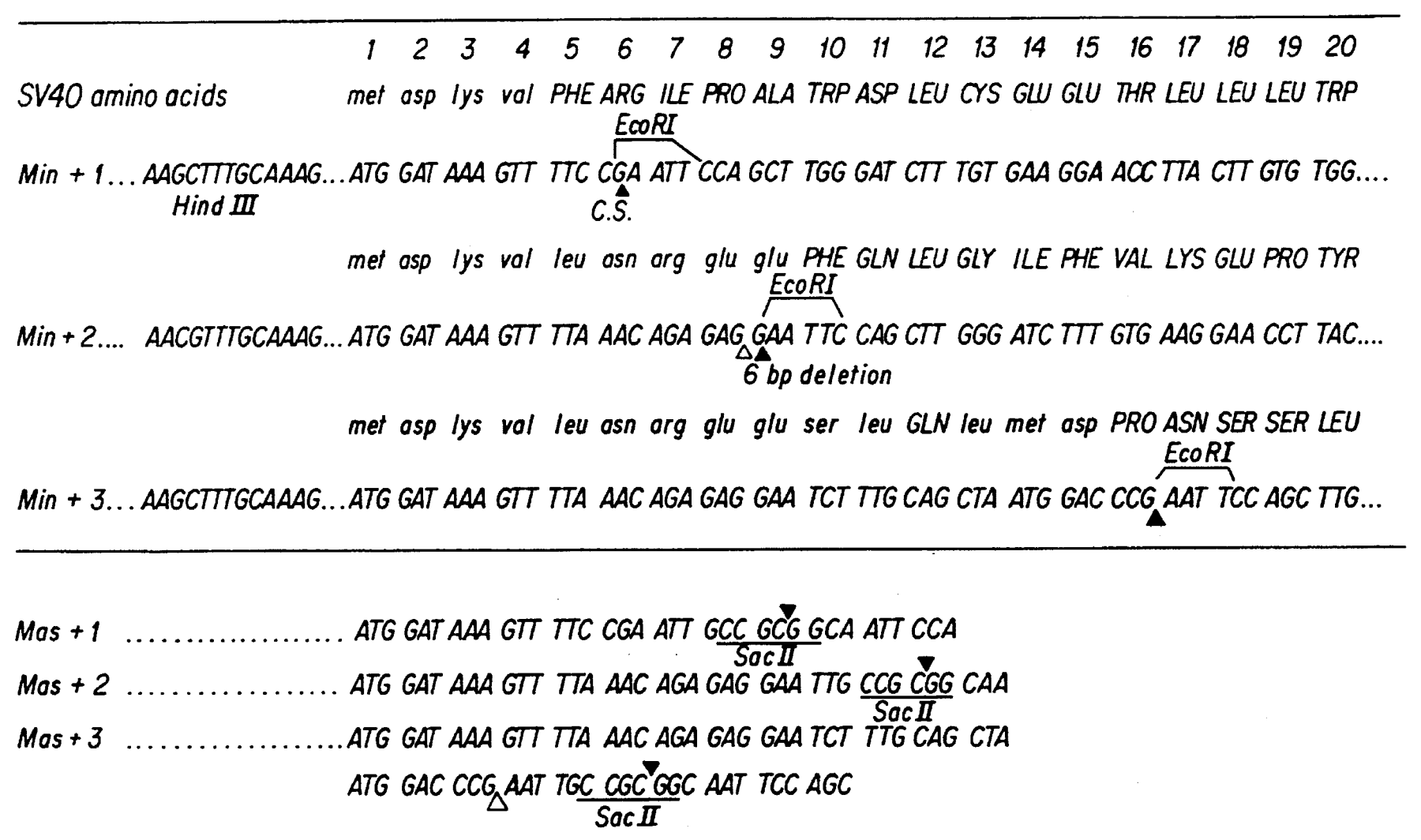

FIG. 8 depicts a comparison of the DNA sequences of the indicated vectors from the unique Hind III site beyond the unique cloning site (C.S.) indicated by black triangles. In the upper panel of FIG. 8, the authentic SV40 coded amino acids are written in small letters starting with the initiation methionine of the SV40 T/t antigens; amino acids written in capital letters represent amino acids coded by the synthetic Eco RI linker followed by vector sequences. An open triangle locates a 6 bp deletion in Min 2. The lower panel of FIG. 8 shows the sequences of the Sac II site that was introduced into Min vectors to produce the Mas vectors 1, 2 and 3. The cloning sites and base pair deletion site are indicated. In other studies, additional sequence analysis data was obtained in the vicinity of the Xba I sites in the aforementioned vectors which show that the Xba I regions remain unmodified, as expected. In Moh and Ameer vectors, the unique Mind III site is destroyed and the JC virus Nco I segment is inserted (see FIG. 7). The sequences around the Eco RI site in Moh and the Sac II site in Ameer are the same as in Min and Mas vectors, respectively.

Figure 9A:
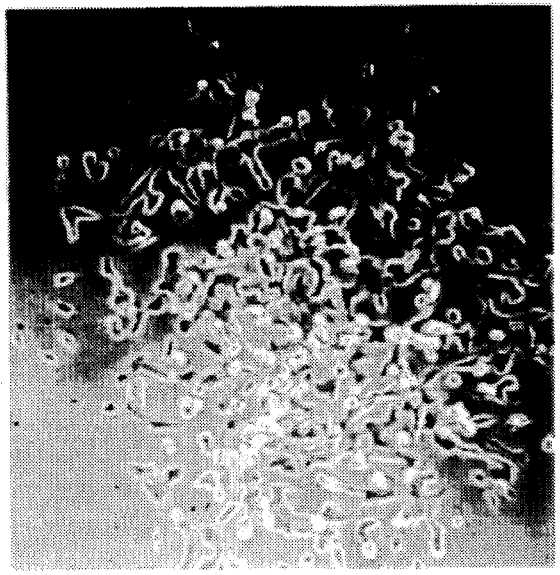
Figure 9B:
Figure 9C:

FIGS. 9A–9C. The indicated cells were transfected with the Min 2 vector, which was linked to the 1.1 kb amy 37 insert containing the A4 region, and were cotransfected with pK0neo (for Genaticin resistance) and pSV$_2$CAT (for the transfection assay). The cells shown survived in the G418 media indicating successful transfection. FIG. 9A: PC12 cells. FIG. 9B: C6 cells. FIG. 9C: Cos A2 cells.

DETAILED DISCUSSION OF THE INVENTION

Definitions

To aid in the understanding of the specification and claims, including the scope to be given such terms, the following definitions are provided.

Gene. A DNA sequence which encodes through its template or messenger RNA a sequence of amino acids characteristic of a specific peptide.

The term cDNA includes genes from which the intervening sequences have been removed. By the term recombinant DNA is meant a molecule that has been recombined by in vitro splicing cDNA or genomic DNA sequence.

Cloning Vehicle. A plasmid or phage DNA or other DNA sequence which is able to replicate in a host cell. The cloning vehicle is characterized by one or a small number of endonuclease recognition sites at which such DNA sequences may be cut in a determinable fashion without loss of an essential biological function of the DNA, which may contain a marker suitable for use in the identification of transformed cells. Markers, for example, are tetracycline resistance or ampicillin resistance. The word "vector" is sometimes used for cloning vehicle.

Expression Vehicle. A vehicle similar to a cloning vehicle but which is capable of expressing a given structural gene in a host, normally under control of certain control sequences.

Expression Control Sequence. A sequence of nucleotides that controls or regulates expression of structural genes when operably linked to those genes. They include the lac systems, the trp system, major operator and promoter regions of phage lambda, the control region of fd coat protein and other sequences known to control the expression of genes in prokaryotic or eukaryotic cells.

Operator. A DNA sequence capable of interacting with the specific repressor, thereby controlling the transcription of adjacent gene(s).

Promoter. A DNA sequence in which RNA polymerase binds and initiates transcription of an adjacent gene(s).

Host. The term "host" is meant to include not only prokaryotes, but also such eukaryotes as yeasts, filamentous fungi, as well as plant and animal cells.

Prokaryote. The term "prokaryote" is meant to include all organisms without a true nucleus, including bacteria.

AD-Amyloid. This term is meant to include polypeptides which are derived from the amyloid of AD brain.

A4-Amyloid. This term is meant to include an A4-amyloid polypeptide from any species, especially from AD human brain (8, 9). The term is also used in this invention to include any analogue, homologue, mutant or derivative of a naturally occurring A4-amyloid. The term is also meant to include fragments having less than the naturally occurring number of amino acids, such as partial fragments of natural A4-amyloid which retain the biological or immunological characteristics of the polypeptide specifically disclosed in this application. The term is also used to include any product which comprises the sequence of a naturally occurring A4-amyloid or analogue thereof, together with one or more flanking amino acids, which still have the same immunologic characteristics.

Products and Processes

The invention comprises the genetic sequences encoding AD-amyloid, vehicles containing the genetic sequence, hosts transformed therewith, AD-amyloid production by transformed host expression, and utilization of AD-amyloid in diagnosis or in therapeutic utilizations.

The DNA sequence coding for AD-amyloid may be derived from a variety of sources, but, in this invention, most particularly from AD brain tissues. Postmortem RNA isolation procedures can be followed (12). For example, mRNA encoded for AD-amyloid may be isolated. The mRNA may then be converted to cDNA by techniques known to those skilled in the art. Probes may be synthesized based on the known amino acid sequence of A4-amyloid peptide.

An AD DNA sequence encoding A4-amyloid may be recombined with vector DNA in accordance with conventional techniques, including blunt-ended or stagger-ended termini for ligation, restriction enzyme digestion to provide appropriate termini, filling in of cohesive ends as appropriate, alkaline phosphatase treatment to avoid undesirable joining, and ligation with appropriate ligases.

To express AD-amyloid, transcriptional and translational signals recognized by an appropriate host element are necessary. Eukaryotic hosts may be mammalian cells capable of culture in vitro, particularly leukocytes, more particularly myeloma cells or other transformed or oncogenic lymphocytes, e.g., EBV-transformed cells. Alternatively, non-mammalian cells may be employed, such as bacteria, fungi, e.g., yeast, filamentous fungi, or the like.

Possible hosts for AD-amyloid production are mammalian cells, grown in vitro in tissue culture or in vivo in animals. Mammalian cells may provide post-translational modifications to AD-amyloid molecules including correct folding or glycosylation of the correct sites. Mammalian cells which may be useful as hosts include cells of fibroblast origin such as VERO or CHO-K1, or cells of lymphoid origin, such as the hybridoma SP2/OAG14 or the myeloma P3×63Sgh, and their derivatives. Usually the AD-amyloid construct Will be part of a vector having a replication system recognized by the host cell.

In one embodiment, a prokaryotic cell is transformed by a plasmid carrying the AD-amyloid encoded gene. Bacterial hosts of particular interest include $E.\ coli$ K12 strain 294 (ATCC 31446), $E.\ coli$ X1776 (ATCC 31537), $E.\ coli$ W3110 (F$^-$, lambda$^-$, prototropic (ATCC 27325)), and other enterobacteriaceaes such as $Salmonella\ typhimurium$ or $Serratia\ marcescens$, and various Pseudomona species. Under such conditions, the AD-amyloid will not be glycosylated. The prokaryotic host must be compatible with the replicon and control sequences in the expression plasmid.

In general, such vectors containing replicon and control sequences which are derived from species compatible with a host cell, are used in connection with the host. The vector ordinarily carries a replicon site, as well as specific genes which are capable of providing phenotypic selection in transformed cells. The expression of the AD-amyloid encoded DNA can also be placed .under control of other regulatory sequences which may be homologous to the organism in its untransformed state. For example, lactose-dependent $E.\ coli$ chromosomal DNA comprises a lactose or lac operon which mediates lactose utilization by elaborating the enzyme β-galactosidase. The lac control elements may be obtained from bacteriophage lambda plac5, which is infective for $E.\ coli$. The lac promoter-operator system can be induced by IPTG.

Other promoter/operator systems or portions thereof can be employed as well. For example, colicin E1, galactose, alkaline phosphatase, tryptophan, xylose, tax, and the like can be used.

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or markers which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cel. Biol.* 3:280 (1983), and others.

A wide variety of transcriptional and translational regulatory sequences may be employed, depending on the nature of the host. The transcriptional and translational signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation signals may also be selected which allow for repression or activation, so that expression of the genes may be modulated. Of interest are regulatory signals which are temperature-sensitive so that by varying the temperature, expression can be repressed or initiated, or are subject to chemical regulation, e.g., metabolite.

Once the vector or DNA sequence containing the constructs has been prepared for expression, the DNA constructs may be introduced to an appropriate host. Various techniques may be employed, such as protoplast fusion, calcium phosphate precipitation, electroporation or other conventional techniques. After the fusion, the cells are grown in media and screened for appropriate activities. Expression of the gene(s) results in production of the AD-amyloid.

The host cells for AD-amyloid production may also be immortalized cells, primarily myeloma or lymphoma cells. These Cells may be grown in an appropriate nutrient medium in culture flasks or injected into a synergistic host, e.g., mouse or rat, or immunodeficient host or host site, e.g., nude mouse or hamster pouch.

The AD-amyloid of the invention may be isolated and purified in accordance with conventional conditions, such as extraction, precipitation, chromatography, affinity chromatography, electrophoresis, or the like.

USES

One application of the cDNA coding for AD-amyloid is for the diagnosis of Alzheimer's disease. The defect causing familial AD is unlikely to be located in or near the amyloid gene (31, 32). Tanzi et al. (31) have suggested that the disorder is either caused by altered expression of a second independent gene on chromosome 21, that may be overexpressed along with the amyloid gene, or by a long range effect of the defect on the expression of the amyloid gene. The latter could arise from a structural abnormality on chromosome 21 causing overexpression of the amyloid gene either by promoting mitotic nondisjunction leading to somatic cells trisomic for this autosome, or by duplication of a large region of the chromosome containing the amyloid gene. One possibility is that the mutation underlying AD may directly alter the expression of the amyloid gene due to a distant cis-acting element (31). Thus, although difficult to prove at the DNA level, overexpression of the amyloid gene may, in some cases, be detectable. In these instances, the amyloid gene of the invention or portions thereof can be labeled and used as probes to develop a test and kit for diagnostic screening.

Another application is the development of cell lines that express the amyloid gene. The value of such cell lines is that they can be used to screen drugs that are potentially useful for treating Alzheimer's disease by stopping the production of amyloid. The latter is assayed by the use of monoclonal antibodies. The single most serious obstacle to developing suitable anti-Alzheimer drugs has been the lack of a suitable biological assay system. The establishment of the cell lines will provide one remedy for the problem.

The availability of transfected cells and transgenic mice carrying an overabundance of the amyloid gene may ultimately serve as the most useful models for the increased deposition of amyloid in the AD brain. One can use the overproduction of a normal gene product, or its synthesis in an unusual cell type, by attaching the mRNA-encoding portion of the gene (cDNA) to novel regulatory sequences (53). Cloned genes that have been introduced into the mouse germ line show appropriate tissue-specific and stage specific patterns of expression (53), despite their integration into apparently random sites in the host genome. Indeed, there is precedent for using the transgenic mouse model to introduce new genes into the mammalian brain and to obtain expression of the genetic product (59). These approaches provide new experimental strategies for answering basic questions in many areas of mammalian biology and allow the production of animal models of human disease. Most specifically, the cells and mice may be the ideal vehicles for evaluating drugs that prevent, or limit the production of amyloid or which increase the degradation of amyloid in vivo. Particularly with respect to neural tissues, the described inventions may be exemplary with regard to elucidating previously unknown aspects of the molecular pathogenesis of AD.

EXAMPLES

EXAMPLE 1 The Cloning of Amyloid cDNA

A. MATERIALS AND METHODS
1. Brain Tissues

Postmortem cortical brain tissues were obtained from the Geriatric Psychiatry Evaluation Clinic at the Massachusetts General Hospital. AD case I was a 67-year-old male (referred to as A67) with a three-to-four-year history of progressive dementia. The clinical diagnosis of Alzheimer's disease was made after neurological, psychiatric, and neuropsychological evaluations. The neuropathological examination was made after a postmortem interval of 2.5 hours and revealed abundant senile plaques and moderate numbers of neurofibrillary tangles in the neocortex with similar changes in the hippocampus and amygdala.

Case II was a 77-year-old male (referred to as A77) with a nine-year history of progressive dementia diagnosed on the same basis as Case I. Abundant neuritic plaques and moderate neurofibrillary tangles were observed throughout the cerebral cortex with similar hippocampal changes. The neuropathological diagnosis was made after a postmortem interval of 4.25 hours.

RNA preparations used for Northern blots were obtained from the above source and from the McLean Hospital Brain Tissue Resource Center.

2. Preparation of RNA

RNA was prepared from cortex as described in reference 12 with the following modifications: (a) frozen tissue was cut on dry ice onto 0.5 g pieces and homogenized in 4.5 volumes of guanidium thiocyanate buffer containing 0.3% antifoam; (b) CsCl was added to the homogenate to a final concentration of 0.15 g/ml; and (c) N-lauryl sarcosine was added to the final concentration of 0.04 g/ml in place of SDS. Poly(A+) RNA was obtained after two purification steps using oligo (dT) cellulose, heat, and denaturing buffers, as described (12).

3. Preparation and Screening of Recombinant cDNA Libraries

Two different lambda-gt11 recombinant cDNA libraries were prepared separately from A67 and A77 postmortem brain poly(A+) RNAs by the general methods previously described (13, 14). After propagation, the A67 library contained $0.5 \times 10^6$ plaques (18% clear). Immunologic screening of the library was conducted (14) to identify the β-galactosidase-AD-amyloid chimera protein using a mixture of monoclonal antibodies (Mabs) made to a synthetic 28-amino-acid polypeptide with the amino acid sequence reported for a plaque amyloid polypeptide referred to as A4 (8). The preparation and characterization of the Mabs are described in copending U.S. Ser. No. 105,751, filed Oct. 8, 1987, and herein incorporated by reference in its entirety.

Positive plaques were isolated after repeated plating. Simultaneously, screening was also carried out using a mixture of three synthetic oligonucleotides corresponding to the A4-amyloid polypeptide sequence (8) as predicted from codon usage: AC(A/G)TC(C/T)TCNGC(A/G)AA(A/G)AA, TG(A/G)TG(A/G)TGNAC(C/T)TC(A/G)TA, CCCACGTCCTCGGCGAAGAACACCAGCT-TCTGGTGGTGCACCTCATA.

After replating, several clones were obtained. One of them, amy10, had an insert of approximately 200 nucleotides that was positive with both the antibody and the oligonucleotide probes. The amy10 insert was subcloned into the pGEM plasmid and partial nucleotide sequences were derived (15). The sequenced molecule demonstrated a region that matched predicted codons of the A4 fetal amyloid amino acids and included nucleotides 1794–1878 (9). The insert as well as a synthetic oligonucleotide based upon the amy10 partial sequence data was synthesized and utilized for screening purposes. A second, and more efficient, cDNA library was prepared from A77 poly(A+) RNA. The amplified library contained $5 \times 10^6$ plaques (50% clear) with inserts sizes of 0.3–2.5 kb. Forty positive clones were identified, thirty of which had inserts of at least 1.0 kb and two with inserts of 1.5 kb or larger. One of these, amy37, was subjected further analysis. The clone amy37 has been deposited before the filing date of the present application at the American Type Culture Collection, Rockville Md., under the terms of the Budapest Treaty and given accession number 40371.

4. Characterization of the Amy37 Recombinant

Restriction enzymology of the recombinant phage DNA was carried out using Eco RI restriction endonuclease and inserts were sized by resolving on 1.2% agarose gels. The amy37 insert was further subcloned into PGEM vectors and sequenced directly using the chemical modification method (15). Amy37 yielded two inserts of approximately 1.1 and 0.5 kb in length that were, in addition, subcloned in the Eco RI site of the M13mp8 vector. The 1.1 kb insert was further digested with Rsa I and subcloned into the Hind II site of M13mp8. Single-stranded DNA prepared from the M13 phages (16) was sequenced by the chain termination method (17) using ($^{35}$S)-dATP and a buffer gradient gel (18). The data were analyzed with a computer program (19).

5. RNA Blot Hybridization

Poly(A+) RNA was twice purified using heat and detergent denaturation steps on oligo(dT) cellulose (12). Samples of 5 μg per slot were resolved on agarose/formaldehyde gels (20), transferred to nitrocellulose membranes, and hybridized. Hybridization was carried out with the amy37 cDNA insert after it was radiolabeled (21) and digested with Eco RI, Pvu II, and Sac I restriction endonucleases to yield probes with an average length of 300 nucleotides. In subsequent experiments, amy37 cDNA was digested with Eco RI restriction endonuclease, subcloned into PGEM vectors, and transcribed in vitro in the presence of α-($^{32}$P)-UTP to obtain riboprobes (22). The latter were used for hybridization where indicated. In some studies, the GFAP insert, GSS-11, was labeled (21) and used for hybridization.

B. RESULTS

1. Identification of amy37: An AD-amyloid insert.

Figure 1:
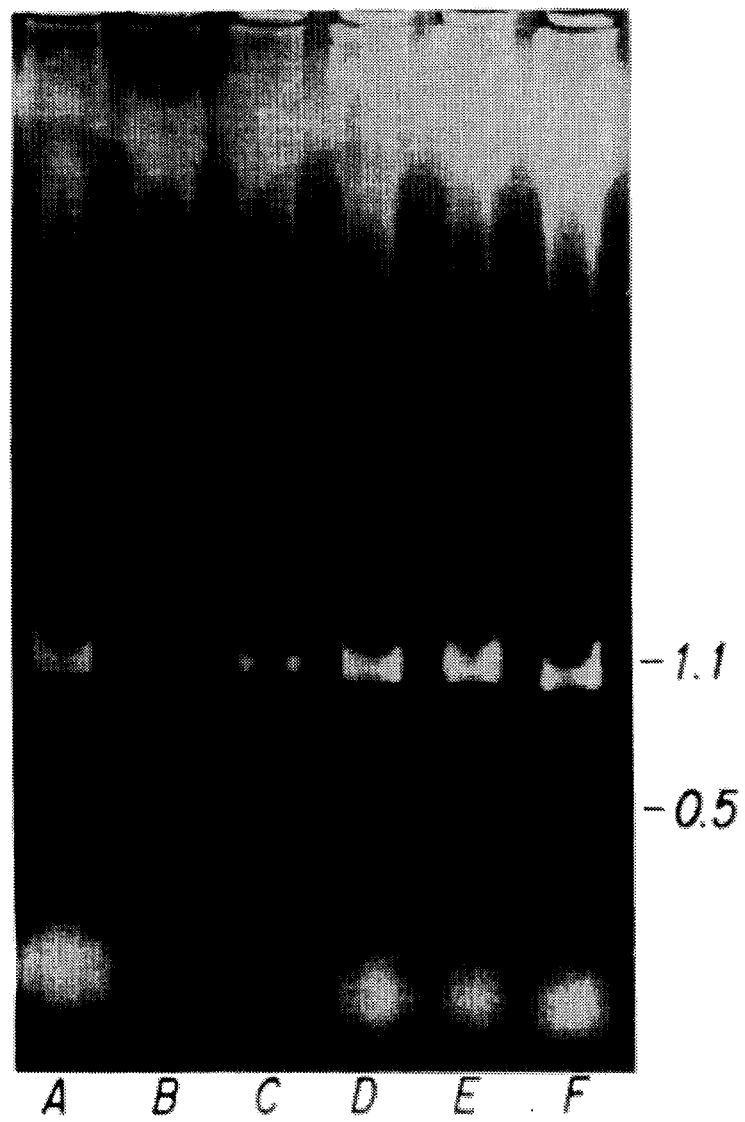
FIG. 1 shows the Eco RI digestion products of lambda gt 11 cDNAs containing A4-amyloid inserts that corresponded to fetal A4-amyloid (9). The bands were resolved on a 1.2% agarose-ethidium bromide gel. Lanes A-E are representative of most inserts obtained; lane F contains the amy37 insert which yielded large and small fragments of the indicated kb sizes.
Figure 2:
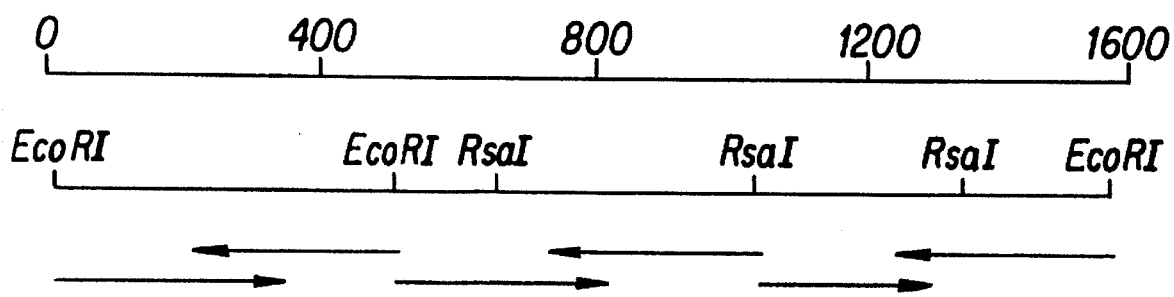
FIG. 2 shows the sequence analysis strategy for the amy37 insert. The fragment of 1564 base pairs were digested with Eco RI and Rsa I and the resulting subfragments were analyzed as described in the Materials and Methods.

The lambda-gt11 cDNA library prepared from Alzheimer case A77 poly(A+) RNA yielded 40 positive recombinant clones after low-density screening. The DNA was isolated from the recombinant phage particles, digested with Eco RI endonuclease, and resolved on a 1.2% agarose-ethidium bromide gel (FIG. 1). Clone amy37 (FIG. 1, lane f) had a cDNA insert consisting of two Eco RI fragments of approximately 1.1 and 0.5 kb derived from the total insert due to an internal Eco RI site (FIGS. 1 and 2). The size of the full-length amyloid precursor cDNA isolated from fresh fetal brain was reported to be 3.2–3.4 kb (9). Thus, the postmortem poly(A+) RNA yielded at least one insert that represented approximately half the length of the fetal precursor molecule.

The cloned insert was subjected to sequence analysis as described in Materials and Methods and summarized in FIG. 2. The derived sequence (FIGS. 3A–3B) matches exactly the corresponding region of the precursor amyloid cDNA sequence derived from the fetal human brain (9). The region encoded by amy37 begins in the translated region at amino acid 431 (using the numbering scheme suggested in reference (9) and includes the A4 amyloid region, consisting of 42 or 43 amino acids, that is deposited in the AD brain (9) (underlined in FIG. 3), and 771 nucleotides of the 3'-non-coding segment.

2. Northern Blot Analyses And Size Estimates of AD Amyloid mRNA

Figure 4:
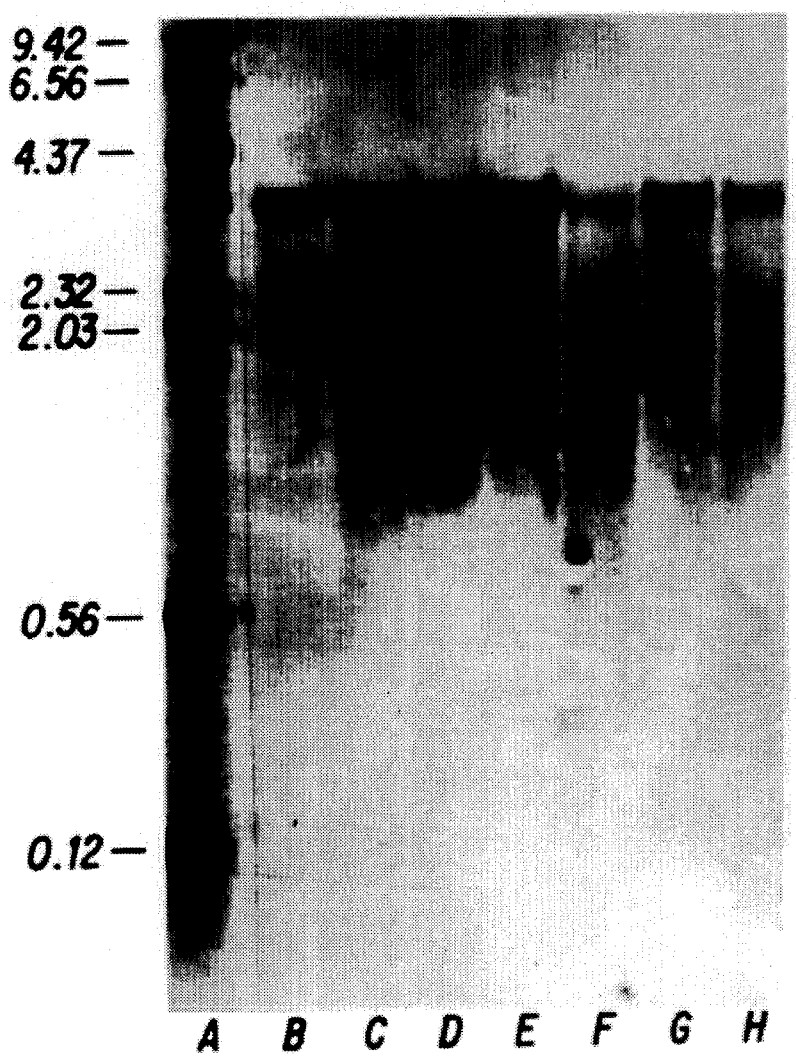
FIG. 4 shows Northern blots of control and AD mRNAs identified with the amy37 probe. Twice purified poly (A+) RNA was subjected to electrophoresis on a formaldehyde-agarose gel and hybridized with the nick-translated amy37 probe.

Northern blot analyses were carried out to compare the amyloid mRNA from control and AD cases. Purified poly(A+) RNA was obtained from control and AD cortices of various ages and postmortem intervals. In all cases a band that spanned the 3.2–3.4 kb range was observed (FIG. 4).

These data establish that the starting mRNA contained the full-length mRNA of AD amyloid. Portions of these data have been published (67).

3. Approach for Making Full-Length AD Amyloid cDNA From AD Brain mRNA

As mentioned earlier, the completely analyzed cDNA clone amy 37 is 1564 nucleotides long (FIGS. 3A–3B). A portion of it codes for the A4 amyloid peptide sequence. FIG. 4 depicts the detailed restriction endonuclease map that includes the amy 37 in addition to flanking restriction enzyme sites deduced from the fetal amyloid cDNA (9). For the purpose of synthesizing the full-length AD-specific amyloid cDNA, a special amyloid mRNA-specific cDNA library was prepared using three different primers for the first strand synthesis.

Primer one (P1) was a synthetic oligonucleotide that corresponds to nucleotide nos. 1795–1883 of amy 37 from the noncoding strand (see FIGS. 3A–3B). The other two primers that were used (P2 and P3) were two short restriction endonuclease fragments generated from amy 37 DNA. Since only three out of approximately 40 recombinants had insert sizes of 1054 b or longer, and in 25 of these molecules the synthesis stopped approximately around nucleotide 1795, the presence of a strong secondary structure in this domain was suspected. To overcome this problem, two approaches were taken: (a) use of methyl mercury hydroxide during the cDNA synthesis (28) and (b) choosing short restriction endonuclease fragments from the region upstream to nucleotide 1795 from amy 37 to be used as primer for synthesis of cDNA on AD amyloid-specific mRNAs. The two primers were as follows: P1 was a 69 base pair long HaeIII-HaeIII fragment extending from nucleotides 1438–1509 (FIGS. 3A–3B); P2 was a 288 base pair long HaeIII-EcoRI fragment extending from nucleotides 1507–1795 (FIGS. 3A–3B). The fragments are indicated schematically in FIG. 5.

The first strand cDNA synthesis was conducted using A77 AD mRNA that had been twice purified through oligo(dT) cellulose, as the template. One of the primers was used in each of three independent reactions as described earlier. The RNA was treated with methyl mercury hydroxide at a concentration of 8 mM for 10 minutes at room temperature and then diluted to 2 mM final concentration. After pooling the single stranded cDNAs synthesized as described (29), a special repair synthesis was thus constructed to produce an amyloid specific cDNA library. A lawn of *E. coli* was transfected with recombinant cDNA molecules at a density of 3000 pfu/150 mm plate and transferred to cellulose nitrate membrane filters as described earlier in this application. Screening of this library was conducted using a probe again isolated from amy 37 DNA. The short probe was a nick-translated EcoRI-PstI restriction endonuclease fragment from amy 37 cDNA harboring nucleotides 1293–1434 (FIGS. 3A–3B, and 5). This probe will allow selection of inserts beyond the suspected site of secondary structure.

FIG. 6A depicts the sizes of cDNA synthesized using this approach. We estimated the size of the transcript needed to reach the 5' end (or at least the AUG initiation codon) at around 1.5 kb. Our cDNA lengths sized on the gels fall into this category. Eleven recombinants were randomly picked which were positive With the short probe after growth on *E. coli*. The phage DNA was then isolated. The DNA was subjected to EcoRI restriction endonuclease analysis to size the inserts and to choose the longest recombinant to finish the repair synthesis and for further characterization by sequence analysis. One of the inserts, amy-x14, had an insert of approximately 1.1 to 1.5 kb (see FIGS. 6A–6C). If the 5' end is not reached, as will be indicated by sequence analysis, then the described procedures will be repeated using appropriate segments of amyx14 as a primer. The amy-x14 clone has been deposited before the filing date of the present application at the American Type Culture Collection, Rockville, Md., under the terms of the Budapest Treaty and given accession number 40370.

4. Construction of a Full-Length AD Amyloid cDNA from Recombinant Amy-37 and Amy-x14 and Additional Inserts.

The repair and joining of the two clones amy-37 and amy-x14 is conducted to produce a full-length AD amyloid cDNA clone as soon as the nucleotide sequence of the amy-x14 at the 3' end is completed. If necessary, this molecule will then be joined to another insert that completely covers the 5' end of the amyloid mRNA. If the 3' terminus of amy-x14 harbors the HaeIII to EcoRI fragment as a primer, then the unique SacI site (FIG. 5) is utilized to join the long EcoRI-SacI fragment of amy-x14 to the SacI-HindIII unique fragment of amy-37 cDNA. If the 3' end of amy-x14 starts at the short HaeIII-HaeIII fragment, then the BamHI approach, described below, is adapted.

The unique BamHI-HindIII fragment of amy-37 is isolated. Similarly, the unique BamHI-BamHI amy-x14 fragment is isolated. The two fragments are ligated together at the BamHI site and molecules with head to tail orientation are isolated using the KPN I and Bal I digestion patterns. The molecules with the head to tail orientation are Klenow repaired to destroy the terminal BamHI and HindIII restriction sites and selected linkers may be added. The cDNA insert is then inserted into vectors for cellular transfection and mouse transgenic experiments.

C. DISCUSSION

Poly(A+) RNA is retained by AD postmortem brains in amounts that are sufficient for functional studies and molecular cloning (12, 24, 25). Northern blot analyses were carried out to compare the AD amyloid mRNA with controls, and then a second mRNA was utilized for further comparisons (see below). The AD cortex contains a doublet at 3.2 and 3.4 kb that is recognized by the amyloid probe. Of three RNA preparations from conventionally obtained AD cases, only one was partly degraded with respect to the full-length mRNA; controls had predominantly intact mRNA. The Northern blots indicated that the levels of AD cortical amyloid mRNA were not typically higher than in controls.

Since cortical neurons are now known to be a rich source of amyloid mRNA (30), the Northern blot results obtained with; the amy37 probe were contrasted to those using a glial-specific probe (data not shown). Human GFAP probe GSS-11, cloned from the A67 cDNA library, corresponds to the coiled-coil α-helical region of the proposed structure for intermediate filaments. No consistent relationship between GFAP and amyloid mRNAs with regard to levels or stability was observed. At the very least the results indicate that variations in these parameters were not exclusively related to random losses associated with premortem or postmortem conditions, or preparative and analytical procedures.

With regard to the low molecular weight species detected by the amy37 probe, it is not immediately apparent that they represent RNAs other than degradation products. However, it has been proposed (26) that inappropriate initiation may occur at methionine 596, which immediately precedes the A4-polypeptide sequence. This formulation is based upon the studies of Kozak (27) who described an optimal sequence for the initiation site of translation by eukaryotic ribosomes as ACCATGG; the latter has key features that maximize activity (the initial A and the terminal G) in common with the nucleotide sequence corresponding to methionine 596 (AAGATGG). Whether internal initiation is possible with regard to the amyloid precursor mRNA, and/or whether the cross-hybridizing species we observed on Northern blots can initiate translation, are currently unknown but merit consideration. The levels of the cross-hybridizing bands varied among the different control and AD samples.

The AD brain is rich in ribonucleases and a combination of transcriptional and degradative factors have been implicated in lowering RNA levels (13). However, the presence of partly degraded RNA in some postmortem preparations may be unrelated to the usual metabolic pathway for RNA turnover. Further, the present studies do not support the view that using only a small number of probes is sufficient to assess the overall intactness of postmortem brain RNA preparations. This is exemplified by comparison of Northern blots using amy37, which revealed apparent degradation products, to those of a GFAP probe, which consistently demonstrated intact glial mRNA. The results indicate that limited Northern blot data are not amenable to generalized conclusions. The observed results may reflect differences in mRNA-specific stability, differences in the susceptibility to degradation of neuronal versus glial RNA in neuropathologic states or as a result of postmortem processes, or a combination of these factors.

The sequence of the amy37 insert derived from the AD brain contains 1564 nucleotides which exactly match 75% of the coding region, and approximately 70% of the 3'-non-coding region of the corresponding fetal brain sequence (9). The present results indicate that nearly one-half the AD precursor is identical to the fetal molecule including the region that is associated with senile plaque cores; this protein segment begins at amino acid 597 and extends for 42 or 43 amino acids (9).

EXAMPLE 2

Preparation of Transfected Eukaryotic Cells

A. Cell Lines

Neuronal, glial and other cell lines are used. These include CosA2, a monkey kidney cell line that has been successfully transformed by SV40 virus (44). The CosA2 cell line is capable of producing low levels of the SV40 T antigen which is needed both for efficient early promotor function as well as replication. Although the early SV40 promotor has been shown to function in a variety of systems, CosA2 is selected as an appropriate positive control. Kidney cells appear to express the amyloid gene, as demonstrated by Northern blot criteria with a probe that included the A4 region (61). HEP G2 is a human liver cell line which has been used to express Factor IX cDNA, the latter was cloned and characterized. Two neuroblastoma cell lines, SKNSH (35) and Lan I (57) are of confirmed neurogenic origin. Rat pheochromacytoma PC12 cells are used since they express neuron-specific marker (neurofilament proteins) particularly in the presence of nerve growth factor (47, 41). The A172 and HS683 cell lines are of confirmed glial origin (43, 52). In the report of Bahmanyar et al. (33) and Kang et al. (9) it was said that amyloid mRNA was detected in certain glial cells of brain.

The above-mentioned cell lines were selected on the basis of preliminary data associated with the ease of transfection with foreign DNA, ease of growth, and their susceptibility to the antibiotic genaticin; these are used as selective genetic markers. In addition, the JC viral control element is used in some experiments to specifically establish AD amyloid cDNA expression in human brain cells. The JC virus, unlike SV40, has a very tight host, tissue, and cellular specificity (42). The virus seems to replicate in human brain. The host range specificity can be eliminated when direct DNA transfections or microinjections are done, but the tissue and cellular specific expression appears to be highly dependent on the enhancer elements and tissue-specific factors.

The decision to utilize co-transfection with selection for genaticin (G418) resistance was based upon the following considerations: (a) selection for a biochemical marker preselects for cells competent for the uptake of DNA (63); (b) the procedure removes from the population spontaneously transformed cells which have not incorporated DNA, for example, in some cells, like NIH 3T3 mouse fibroblasts, the mere physical presence of calcium phosphate precipitated DNA can induce morphologically altered foci; (c) cells which incorporate a selectable marker are likely to have incorporated an average of $3 \times 10^3$ kb from the coprecipitated DNA. A total of $10^3$ G418 resistant colonies would likely have incorporated in total $3 \times 10^6$ kb of coprecipitated DNA which is about a genome equivalent.

B. Generation of Eukaryotic Cell Vectors Transfected With AD Amyloid cDNA Sequences The approach is to transfect various cell lines, e.g., neuronal, glial, kidney and liver with the amyloid cDNA using heterologous regulatory elements.

For any gene expression to occur, the appropriate gene expression control elements are needed. These are eukaryotic or prokaryotic, homologous or heterologous. Especially when one wishes to express eukaryotic cDNA copies of the eukaryotic genes in eukaryotic host systems, transcriptional and translational signals recognized by appropriate host elements are essential.

At present, the homologous promotor and control elements for β-amyloid gene expression have not been isolated and characterized. For the purpose of immediate investigations, the heterologous control regions derived from the SV40 and JC viruses are used. The decision to choose SV40 regulatory elements vs. other viral control elements (e.g., papilloma or retroviruses) is based upon the following considerations: (a) SV40 control elements are the best studied; (b) they have been used to express a variety of cDNAs in a wide variety of cell lines; (c) our research, for over a decade, has involved a major portion of the original molecular biological studies of SV40 which involved characterizing and analyzing the viral genome and defining promoters, terminators, etc. (e.g. see: 50, 60 and 68).

The SV40 based vectors, described below, were chosen to link with the amy37 cDNA insert. A very similar vector without the insert, pKO+neo, but harboring an antibiotic resistant gene for Geniticin, is used as a cotransfectant marker. The transfected cells are grown in a medium containing Geniticin. The transfected cells expressing the brain amyloid, and resistant to Geniticin, are cloned, characterized, propagated, and further developed into established cell lines according to Fasano, et al. (40).

The starting vector pKo+RIML is composed of $PML_2$ (a derivative of pBR322 lacking sequences poisonous for monkey kidney cell replication), the Lac $UV_5$ promotor of E. coli and SV40 sequences covering the enhancer, origin of replication, early promotor, small "t" antigen splice sites and polyadenylation sites (FIGS. 7A–7B). FIG. 8 compares DNA sequences flanking the unique cloning sites of the described vectors. The modification of the existing plasmid was done in such a way that the 3 variant plasmids contained one of the 3 segments of SV40 sequences all starting at the Bgl I site but terminating at different positions within the SV40 t/T coding region covering all 3 potential translating frames. The schematic diagram for this construction is depicted in FIGS. 7A–7B.

The vectors are as follows: (a) Min 1, 2 and vectors which read in the three frames starting from the SV40 T antigen; these can be used for inserting cDNA cut with Eco R1 (the amyloid precursor cDNA has internal Eco RI sites as shown by Kang et al., (9) and Zain et al., (65, 66). Of further importance is that the two Xba sites in the Min vectors separate the eukaryotic sequences from the prokaryotic regions. The Xba sequence is not present as an internal restriction site in AD amyloid cDNA); (b) Mas 1, 2 and 3 vectors contain a unique Sac II site in lieu of the Eco RI cloning site for expressing the full length amyloid cDNA; (c) vectors with the JC virus control elements that may have preference for human brain cell transfections, referred to as Moh 1, 2, 3 and Ameer 1, 2, 3, are described subsequently.

The SV40 enhancer, promotor and DNA replication origin region are replaced with human JC virus control elements to produce the Moh and Ameer vectors (FIGS. 7A–7B). The JC virus causes Progressive Multifocal Leukoencephalopathy, a progressive demyelinating brain disease. The JC virus has a structure very similar to SV40 virus, but has a very tight host and tissue specificity range (42). By transfecting the cells with the derived DNA, the species barriers can be eliminated, but the tissue-specific expression is highly dependent on the enhancer elements (69). Therefore, the SV40 enhancers, promotor, DNA replication origin region of the Min 1, 2, 3 and Mas 1, 2, 3 vectors are replaced to generate the new vectors i.e., the Moh and Ameer series. All vectors are characterized by restriction enzyme analysis, sequence analysis (FIG. 8) and transfection competency. The diagrammatic schemes for such vector constructions is shown in (FIGS. 7A–7B).

The Min, Mas, Moh and Ameer vectors are suitable for the transgenic mouse studies as well as the cellular transfection studies. Xba I digestion of the recombinants separates bacterial sequences, harmful to eukaryotic gene expression, from the AD amyloid gene, especially for microinjection into mouse fertilized eggs.

C. Cloning of the β-amyloid (A4) peptide-encoding domain into expression vectors for transfection experiments The insert from Amy37 DNA was isolated by digestion with the EcoRI restriction endonuclease; the resulting large 1.1 kb fragment (see Example 1) was subcloned into the Min 1, 2 and 3 vectors and used to transfect various cells in tissue culture. The cells were co-transfected with the Geniticin resistance gene and the CAT gene (see below) and surviving colonies were isolated. Shown in FIG. 9 are surviving PC12, C6 and Cos A2 cells.

D. Initial transfection experiments (1) Establishment of optimal conditions for transfection In general, DNA transfections are carried out using modifications of the basic technique of Graham & Van der Eb (46). The cells are cotransfected with plasmids carrying the CAT (chloramphenicol acetyl transferase) gene and its expression product measured as a function of transfection. Typical CAT assays are shown in Table I. To improve the transfection efficiency and establish the optimal transfection protocol, various methods of transfection are used, e.g., using $CaPO_4$ or DEAE dextran to precipitate the transfecting DNA. The protocols are described below. In initial studies CosA2, HS683, A172 and HepG2 all gave satisfactory results using the $CaPO_4$ method. CosA2 responded equally well to DEAE dextran precipitation. With SKNSH, some transfection was observed. In addition, $C_6$ and PC12, two mouse cell lines, appear positive in initial transfection studies.

Variations in each method, i.e., glycerol or chloroquine for shock treatment and sodium butyrate to enhance DNA incorporation or expression, were also tested. Overall, chloroquine shock appears to be better than glycerol. The following parameters are taken into account prior to transfection experiments: (i) The effects of differing amounts of sodium butyrate on different cell lines, and also differing amounts of chloroquine, and (ii) amounts of DNA needed to optimize transfections.

(2) Analysis of transfected cells

Transfection efficiency was checked using the CAT assay (Table I). Immunostaining of transfected cells using the mixture of A4 amyloid mabs (see copending application, Ser. No. 105,751 (U.S. Pat. No. 5,231,000), filed Oct. 8, 1987, incorporated by reference herein in its entirety) is done to check for overproduction of β amyloid (A4) peptide. The results of immunostaining experiments are being confirmed by transfecting larger number of cells, isolating the proteins synthesized and detecting the A4 peptide by Western blot analysis using the mab antibodies mentioned above. As a measure of transcriptional capacity of the newly integrated gene, in situ hybridizations are carried out on transfected cells and control mock transfected cells using high specific activity Amy37 insert riboprobes (55, 66). These data are further confirmed by Northern blot analysis of the mRNA using amyloid specific cDNA probes from Amy37 inserts (see Example 1).

(3) CAT assays to assess transfection efficiency

This assay is conducted using a modified protocol described by Gorman et al. (45). In general, cell extracts are prepared by suspending $10^6$ cells in 100 μl of 0.25M Tris, pH 8, freeze and thaw×3, centrifuge and use the supernatant 10 μl of cell extract, 9.75 μl of 0.25M Tris/HCl, pH 7.8, 4 μl of $^{14}C$ chloramphenicol (Amersham) (0.1 μl) and 1.25 μl 40 mM Acetyl COA are mixed, incubated at 37° C. for an hour, and extracted with ethylacetate (0.3 ml). The ethylacetate is evaporated, the residue resuspended in 15 μl of ethylacetate and spotted on TLC paper. Ascending chromatography is performed using chloroform/methanol solvent. The paper chromatogram is autoradiographed overnight. The results of such experiments are depicted in Table I.

(4) Establishment of optimal conditions for isolating G418 resistant transfected cells The first step in this process is to titrate the optimal amount of genaticin needed to kill the cells. Since each cell type has a different degree of resistance towards genaticin, HS683, HepG$_2$, CosA$_2$, and SKNSH cells were titrated at 0–0.6 gm/liter of genaticin in the media and the level of survival of these cells was measured on each day following drug treatment. Both the glial (HS683) and neuronal (SKNSH) cells responded very well to the drug between 0.2–0.4 gm/liter concentration. These experiments were repeated for the human liver (HepG2), kidney (CosA2), C6 mouse glioma and PC12 mouse cells.

E. Assay of amyloid overproduction

Cells are monitored by anti-amyloid antibodies for the overproduction of amyloid (see copending application, Ser. No. 105,751 (U.S. Pat. No. 5,231,000), filed Oct. 8, 1987).

TABLE I

Transfection of CosA$_2$ cells with pSV$_2$CAT (E) and Control Salmon Sperm DNA (c) using either CaPO$_4$ or DEAE dextran method:

| Treatment: | %$^{14}$C-chloramphenicol converted to mono & diacetyl derivatives | | | |
|---|---|---|---|---|
| | E$_1$ | C$_1$ | E$_2$ | C$_2$ |

| 3 hour transfection with | DEAE-Dextran | | CaPO$_4$ | |
| --- | --- | --- | --- | --- |
| E or C | 88,91 | 2.0 | 65,62 | <1 |
| + Glycerol shock | 96,96 | 1.0 | 94,96 | <1 |
| + Glycerol + Butyrate | 88,82 | <1.0 | — | — |
| + Chloroquine | 95,92 | <1.0 | 96,90 | <1 |
| Modified procedure | 86,84 | 3.0 | — | — |
| CAT | 0.1 unit 95% conversion | | 0.5 unit gives 99,964 conversion | |
| | 0.5 unit 86% conversion | | | |
| | 0.025 unit 73% conversion | | | |

(Data from 2 independent expseriments $E_1$ and $E_2$ is shown. pSV2 CAT is used in experiment (E) and Salmon Sperm in controls (C).)

F. Immunologic and in situ hybridization studies

Immunologic and in situ hybridization protocols using antibody probes for the characterization of cells and transgenic mice are carried out by previously described methods (38, 49, 34).

G. Transgenic mouse protocol

Initially, the same vectors described for transfection studies, Min, Mas, Moh and Ameer, are used and applied towards the preparation of transgenic mice. For microinjection work, it is very important to eliminate the bacterial sequences which can be poisonous for eukaryotic cell replication (48). The exact nature of these sequences is not known, except for a region from plasmid pBR322, which has been eliminated in the pko-vector series (the precursors of the Min, Mas, Moh and Ameer vectors), which are poisonous for monkey kidney cells. Therefore, the vectors are designed in such a way that eukaryotic sequences can be easily separated (by digestion with Xba I enzyme) from the prokaryotic sequences. The aim is to generate animals that express only subdomains of the amyloid precursor (A4 and non-A4 domains using Min and Moh vectors); or, in the total precursor cDNA harboring either SV40 control elements, or JC control elements (Mas and Ameer vectors). Expression may occur in neurons or glia. Although initial studies make use of vectors derived from SV40, other studies use neuron-specific regulatory elements. These elements are the portions of the genome that contain the control region of neurofilament protein expression or the β-amyloid gene's natural control region isolated from AD genomic libraries.

Various factors affect the frequency of integration. These include the form of DNA (linear vs. supercoiled), its purity, concentration and the buffer in which the DNA is dissolved. Each of these factors are addressed as the experiments proceed. For example, the DNA for microinjection should be free of all contaminants that might harm the egg; e.g., phenol, ethanol, enzymes and particulate matter (that may clog the injection needle). Therefore, the DNA is purified thoroughly by CsCl$_2$ density gradient centrifugation (see below), and prior to microinjection, all samples are filtered through 0.2 µm filters. For initial experiments, 100 µg of DNA insert (containing only eukaryotic sequences) is isolated by restriction endonuclease digestion followed by agarose gel electrophoresis, and purification by passage through a DEAE-sepharose column. At this-point, the CsCl$_2$ purification is utilized. 10 µg of the DNA insert is dissolved in 2.4 ml of 10 mM Tris, pH 7.9, 1 mM EDTA and exactly 3 gms of ultrapure CsCl is added. After dissolving the CsCl, the density of the solution is checked to make sure it is 1.70±0.01 gm/ml. The solution is transferred to a clean 1.3×5 cm polyallomer ultracentrifuge tube, covered with light paraffin oil and centrifuged for 48 hours in a SW50.1 rotor at 20° C. and 40,000 rpm. 0.2 ml fractions are carefully collected from the bottom of the tube, and the middle 8 tubes are assayed for DNA by running 2 µl on a miniagarose gel. Fractions containing the purified DNA are pooled and dialyzed against a large volume of injection buffer (10 mM Tris, pH 7.4, 0.2 mM EDTA) changing the buffer several times over a 48 h period. The DNA concentration is adjusted to 5 µg/ml, aliquoted into sterile Eppendorf tubes, lyophilized and stored at −20° C.

The night before injections, appropriate amounts of water are added and left in the refrigerator to dissolve the lyophilized DNA and reconstitute it to an appropriate volume. C57 BL/6J (the inbred stain of mice) is the choice strain. The F2 zygotes from these animals are used for microinjections. Fertilized eggs are obtained by superovulating the females. 1–2 picoliter of highly purified DNA (2–5 µg/ml in injection buffer) is injected into the pronuclei of fertilized eggs. The pronuclei of fertilized eggs swell progressively during the one cell stage and are in an optimum stage for injections during a period of 3.5 hours. After all the eggs are injected, sorting is done to separate the healthy eggs from the lysed ones. The healthy eggs are cultured in vitro for 3–5 days until they have reached the blastocyte stage, in $M_2$ media (36). The recipient female mice, 6–8 weeks old and weighing 20 gm, are mated to vasectomized males at least 2.5 days before the transfer. The animals are maintained in a constant light-dark cycle (7 p.m.–5 a.m. dark, 5 a.m.–7 p.m. light).

To set up matings, females (6 weeks, 4 months old) are examined in the afternoon and those in estrus are placed with males (1–2 females with 1 male/cage). The morning after, the females are checked for copulation plug in the vagina. Uterine transfers of the blastocyst stage embryos are conducted in 6–8 week old female $F_1$ hybrids (C57BL/6 xCBA) mated to vasectomized males. Each recipient gets 7–8 embryos transferred in her uterine horns to get a litter size of at least five.

The fertilized eggs are dissected out several hours before they are to be injected. A 4–6 week old superovulated female (B6XCBA F1) generally yields 20–30 eggs. The abdominal cavity is opened, the oviduct and ovary is pulled out, and cut between the oviduct and ovary. The oviduct and the attached segment of the uterus are transferred to a 35 mm petri dish containing M2 media at room temperature. In a separate 35 mm petri dish,. M2 medium containing 300 µg/ml of hyaluronidase is placed at room temperature. While viewing through a stereomicroscope, the eggs are pushed out gently by squeezing the oviduct with blunt forceps and allowed to incubate until the cumulus cells fall off. The eggs are rinsed to get rid of the enzyme and transferred to a fresh dish of M2 within 1–2 minutes after the cumulus falls. The eggs are transferred to M16 media for culture at 37° C. and incubated to get 3.5 day blastocysts. M16 is a modified Krebs-Ringer bicarbonate solution which is very similar to Whittens medium (62).

H. Detection of the integrated amyloid cDNA and its expression products in the transgenic mice and establishment of transgenic mouse lines Identification of the homozygous transgenic mice is done as follows. Southern blot analysis is performed on tail DNA using two probes: (a) the 3' end noncoding sequences of the mouse A4 amyloid cDNA to check for endogenous gene copy numbers and (b) the AD human A4 amyloid cDNA sequences from a similar region as a marker for the integrated gene. The intensity of band(s) representing the foreign DNA is compared with that of band(s) from the endogenous gene using densitometry of the autoradiogram. In addition, the homozygosity of each animal is confirmed first by genetic means, because quantitative methods for homozygotes can produce erroneous results. Therefore, each presumptive homozygous mouse is crossed with a nontransgenic mouse and checked for 100% transmission of the foreign DNA to the progeny.

Karyotyping of mouse cells and mapping integrated genes to chromosomes in situ by hybridization is conducted as described earlier for more precise localization of the factor IX gene on the X chromosome (54). The two probes used are those mentioned above used to differentiate between endogenous and integrated cDNA.

Localization of gene transcripts in various tissue sections is conducted after sacrificing the male founder mice (the animals are sacrificed only after each has plugged at least 6–8 females). To avail kidney and spleen tissues, partial nephrectomy and splenectomy is conducted, but for brain sections, it is essential to sacrifice the animals.

I. Characterization of the transaenic mice

These studies are carried out concurrently with human postmortem neuroanatomic investigations. After determining that a transgenic line is established, the animals are sacrificed, sections of their tissue are utilized for neuroanatomical studies and the remainder for neurochemical and biochemical studies, i.e., gene copy number, transcriptional and translational analysis, gene dissections, etc.

J. Development of the transgenic line

Mice that develop from injected eggs are called "founder" mice. After identifying the founder, transgenie matings are started to establish a transgenic line. The male founder is placed with two females, which are checked each day and replaced with new females as soon as each is plugged. In this manner, the male can sire many litters within a few weeks. As soon as a male has plugged 6–8 females, he is sacrificed, if necessary, for the analysis of gene expression. In the case of female founders, after she has given birth and raised at least several litters, she is sacrificed for analysis of gene expression. None of the animals are sacrificed until positive transgenic progeny are identified. Once the line is established and biochemical and neuroanatomical analysis conducted for amyloid integration and its expression, then other Studies like behavioral, neurophysiological, etc., are conducted to identify the various lesions generated in the animals due to different site integration and expression of the β amyloid gene.

REFERENCES

1. Wisniewski, H. M., and Terry, R. D. (1973) in *Progress in Neuropathology* (Zimmerman, H. M., ed.), pp. 1–26, Grune and Stratton, New York.
2. Roth, M., et al., (1966) *Nature* 209:109–110.
3. Blessed, G., et al., (1968) *Nature* 114:797–811.
4. Metz, P. A., et al., (1983) *Acta Neuropathol.* (Berl.) 60:113–124.
5. Glenner, G. G. (1980), *N. Engl. J. Med.* 302:1333–1343.
6. Glenner, G. G., and Wong, C. W. (1984), *Biochem. Biophys. Res. Commun.* 120:885–890.
7. Glenner, G. G., and Wong, C. W. (1984), *Biochem. Biophys. Res. Commun.* 122:1131–1135.
8. Masters, C. L., et al. (1985), *Proc. Natl. Acad. Sci. USA* 82:4245–4249.
9. Kang, J., et al. (1987), *Nature* 325:733–736.
10. St. George-Hyslop, P., et al. (1987), *Science* 235:885–890.
11. Tanzi, R. E., Gusella, J. G., Watkins, P. C., Bruns, G. A. P., St, George-Hyslop, P., Van Keuren, M. L., Patterson, D., Pagan, S., Kurnit, D. M. and Neve, R. L., (1987), *Science* 235:880–884.
12. Sajdel-Sulkowska, E. M., et al. (1983), *J. Neurochem.* 40:670–680.
13. Marotta, C. A., et al. (1986), *Prog. Brain Res.* 70:303–319.
14. Young, R., and Davis, R. (1983), *Proc. Natl. Acad. Sci. USA* 80:11914–1198.
15. Maxam, A. M., and Gilbert, W. (1980), *Methods Enzymol.* 65:499–560.
16. Messing, J. (1983), *Methods in Enzymology* 101:20–78.
17. Sanger, F., et al. (1977), *Proc. Natl. Acad. Sci. USA* 74:5463–5467.
18. Biggin, M. D., et al. (1983), *Proc. Natl. Acad. Sci. USA* 80:3463–3965.
19. Staden, R. (1980), *Nucleic Acids Res.* 8:3673–3694.
20. Thomas, P. S. (1980), *Proc. Natl. Acad. Sci. USA* 77:5201–5205.
21. Rigby, P. W. J., et al. (1977), *J. Mol. Biol.* 113:237–251.
22. Angerer, R., et al. (1985), *Genetic Engineering. Principles and Methods* 7:43–65.
23. Lewis, S. A., .et al. (1984), *Proc. Natl. Acad. Sci. USA* 81:2743–2746.
24. Marotta, C. A., et al., American College of Neuropsychopharmacology Satellite Meeting (Dec. 10, 1979) in *Genetic Research Strategies in Psychobiology and Psychiatry* (Gershon, E. S., Matthysse, S., Breakefield, X. O., and Ciarnanello, R. D., eds.), pp. 39–58.
25. Marotta, C. A., et al. (1981), *J. Neurochem.* 36:966–975.
26. Breimer, L. H., and Denny, P. (1987), *Nature* 326:749–750.
27. Kozak, M. (1986), *Cell* 44:283–292.
28. Payvar, F. and Schimke, R. T., *J. Biol. Chem.* 254:7636 (1979).
29. Polites, H. G. and Marotti, K. R., *Biotechniques* 4:514–520 (1986).
30. Salim, M., Zain, S. B., Chou, W.-G., Saidel-Sulkowska, F. M., Majocha, R. E., Rehman, S., Benes, F. M. and Marotta, C. A. (1987a) Molecular cloning of amyloid cDNA from Alzheimer brain messenger RNA. Correlative neuroimmunologic and in situ hybridization studies. In: J. P. Blass, G. D. Miner, L. A. Miner, R. W. Richter and J. L. Valentine (eds.) *Familial Alzheimer's Disease: Molecular Genetics, Clinical Prospects and Societal Issues*, Marcel Dekker, N.Y., in press.
31. Tanzi, R. E., St. George-Hyslop, P. H., Haines, J. L., Polinsky, R. J., Nee, L., Foncin, J.-F., Neve, R. L., McClatchy, A. I., Conneally, P. M. and Gusella, J. F., *Nature* 329.:156–157.
32. Van Broeckhoven, C., Genthe, A. M., Vandenberghe, A., Horsthemke, B., Backhovens, H., Raeymaekers, R., Van Hul, W., Wehnert, A., Gheuens, J.,. Cras, P., Bruyland, M., Martin, J. J., Salbaum, M., Multhaup, G., Masters, C. L., Beyreuther, K., Gurling, H. M. D., Mullan, M. J., Holland, A., Barton, A., Irving, M., Williamson, R., Richards, S. J., and Hardy, J. A. (1987), *Nature* 329:153–157.
33. Bahmanyar, S., et al., *Science* 327:77–80 (1987).
34. Benes, F. M., et al., Structural diversity and infrastructure of amyloid deposits in Alzheimer brain. Society for Neurosciences (Abstracts) 13:1151 (1987).
35. Biedler, J., et al., *Cancer Res.* 33:2643–2652 (1973).
36. Biggers, J. D., et al. (1971) The culture of mouse embryos in vitro. In: Methods in Mammalian Embryology, (ed., J. C. Daniel), pp. 86–116, W. H. Freeman, San Francisco.
37. Blessed, G., et al., *Br. J. Psychiatry* 114:797–811 (1968).
38. Brown, B. A., et al., *Neurochem.* 40:299–308 (1983).
39. Delabar, J. -M., et al., *Science* 235: 1390–1392 (1987).
40. Fasano, O., et al., *Mol. Cell Biol.* 4:1695–1701 (1984).
41. Franke, W. W., et al., *J. Cell Biol.* 103: 1933–1943 (1986).

42. Frisque, R. J., et al., *J. Virol.* 51:458–469 (1984).
43. Giard, D. J., et al., *J. Natl. Cancer Inst.* 51:1417–1421 (1973).
44. Gluzman, Y., *Cell* 23:175–182 (1981).
45. Gorman, C., et al., *J. Mol. Cell. Biol.* 2:1044–1051 (1982).
46. Graham, F. L., et al., *Virology* 52:456–467 (1983); Hofstein, R., et al., *Ann. N.Y. Acad. Sci.* 455:787–789 (1983).
47. Lindenbaum, M. H., et al., *J. Biol. Chem.* 262:605–610 (1987).
48. Lusky, M., et al., *Nature* 293:79–81 (1981).
49. Majocha, R. E., et al., *Can. J. Blochem. Cell Biol.* 63:577–584 (1985).
50. Marotta, C. A., et al., *Methods in Enzymology* 24:254–272 (1974).
51. Masters, C. L., et al., *Proc. Natl. Acad. Sci. (U.S.A.)* 82:4245–4249 (1985).
52. Owens, R. B., et al., *J. Natl. Cancer Inst.* 56:843–849 (1976).
53. Palmiter, R. D., et al., *Nature* 300:611–615 (1982).
54. Quirk, S., et al., *Cytogen. Cell Gen.* 39:212–224 (1984).
55. Sajdel-Sulkowska, E. M., et al., *Abstracts, Society for Neuroscience* 12:1400 (1986).
56. Sajdel-Sulkowska, E. M., et al., The postmortem Alzheimer brain is a source of structurally and functionally intact astrocytic messenger RNA. *J. Neurosci. Methods*, in press (1987).
57. Seeger, R. C., et al., *Cancer Res.* 37:1364–1371 (1977).
58. St. George-Hyslop, P. H., et al., *Science* 238:664–666 (1987).
59. Stout, J. T., et al., *Nature* 317:150–152 (1985).
60. Subramanian, K. N., et al., *Prog. Nucl. Acid Res. Mol. Biol.* 19:157–164 (1976).
61. Tanzi, R. E., et al., *Science* 235:880–884 (1987).
62. Whitten, W. K., et al., *J. Reprod. Fertil.* 17:399–401 (1968).
63. Wigler, M., et al., *Cell* 16:777–785 (1979).
64. Wisniewski, H. M., et al., Reexamination of the pathogenesis of the senile plaque. In: H. M. Zimmerman (ed.), *Progress in Neuropathology*, pp. 1–26, Grune and Stratton, New York (1973).
65. Zain, S. B., et al., *Society for Neurosciences* (Abstracts) 13:558 (1987).
66. Zain, S. B., et al., Molecular cloning of amyloid cDNA derived from mRNA of the Alzheimer brain. Coding and non-coding regions of the fetal precursor mRNA are expressed in the Alzheimer cortex. *Proc. Natl. Acad. Sci. (USA)* 85:929–933 (1988).
67. Zain, S. B., et al., *J. Cell. Biochem.* (UCLA Symposia on Molecular and Cellular Biology), Suppl. 11D, abs. S415, 198 (1987).
68. Zain, S. B., et al., *J. Biol. Chem.* 253:1606–1612 (1978).
69. Zinn, K., et al., *Proc. Natl. Acad. Sci. (USA)* 79:4897–4901 (1982).

---

What is claimed is:

1. An in vitro method for screening drugs that are potentially useful for treatment of Alzheimer's disease which comprises (a) contacting a drug with a host transformed with a DNA construct, wherein said DNA construct comprises a DNA sequence encoding human A4 amyloid peptide and said construct overexpresses said peptide and (b) detecting limitation or prevention of production or increased degradation of said peptide due to said drug.

2. The method of claim 1 wherein said host is a eukaryotic cell line in vitro.

3. A method for screening drugs that are potentially useful for treatment of Alzheimer's disease as claimed in claim 1, wherein said DNA construct contains a sequence encoding A4-amyloid peptide.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: both ( x i ) SEQUENCE DESCRIPTION: SEQ ID NO:1:

```
ACRTCYTCNG CRAARAA                                                17
```

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: both ( x i ) SEQUENCE DESCRIPTION: SEQ ID NO:2:

```
TGRTGRTGNA CYTCRTA                                                17
```

( 2 ) INFORMATION FOR SEQ ID NO:3:

( i ) SEQUENCE CHARACTERISTICS:
        ( A ) LENGTH: 47 base pairs
        ( B ) TYPE: nucleic acid
        ( C ) STRANDEDNESS: both
        ( D ) TOPOLOGY: both ( x i ) SEQUENCE DESCRIPTION: SEQ ID NO:3:

```
CCCACGTCCT CGGCGAAGAA CACCAGCTTC TGGTGGTGCA CCTCATA              47
```

( 2 ) INFORMATION FOR SEQ ID NO:4:

( i ) SEQUENCE CHARACTERISTICS:
        ( A ) LENGTH: 1564 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: 2..796

( x i ) SEQUENCE DESCRIPTION: SEQ ID NO:4:

```
G CAC ACC CTA AAG CAT TTC GAG CAT GTG CGC ATG GTG GAT CCC AAG        46
  His Thr Leu Lys His Phe Glu His Val Arg Met Val Asp Pro Lys
  1               5                   10                  15

AAA GCC GCT CAG ATC CGG TCC CAG GTT ATG ACA CAC CTC CGT GTG ATT       94
Lys Ala Ala Gln Ile Arg Ser Gln Val Met Thr His Leu Arg Val Ile
                20                  25                  30

TAT GAG CGC ATG AAT CAG TCT CTC TCC CTG CTC TAC AAC GTG CCT GCA      142
Tyr Glu Arg Met Asn Gln Ser Leu Ser Leu Leu Tyr Asn Val Pro Ala
            35                  40                  45

GTG GCC GAG GAG ATT CAG GAT GAA GTT GAT GAG CTG CTT CAG AAA GAG      190
Val Ala Glu Glu Ile Gln Asp Glu Val Asp Glu Leu Leu Gln Lys Glu
        50                  55                  60

CAA AAC TAT TCA GAT GAC GTC TTG GCC AAC ATG ATT AGT GAA CCA AGG      238
Gln Asn Tyr Ser Asp Asp Val Leu Ala Asn Met Ile Ser Glu Pro Arg
    65                  70                  75

ATC AGT TAC GGA AAC GAT GCT CTC ATG CCA TCT TTG ACC GAA ACG AAA      286
Ile Ser Tyr Gly Asn Asp Ala Leu Met Pro Ser Leu Thr Glu Thr Lys
80                  85                  90                  95

ACC ACC GTG GAG CTC CTT CCC GTG AAT GGA GAG TTC AGC CTG GAC GAT      334
Thr Thr Val Glu Leu Leu Pro Val Asn Gly Glu Phe Ser Leu Asp Asp
                100                 105                 110

CTC CAG CCG TGG CAT TCT TTT GGG GCT GAC TCT GTG CCA GCC AAC ACA      382
Leu Gln Pro Trp His Ser Phe Gly Ala Asp Ser Val Pro Ala Asn Thr
            115                 120                 125

GAA AAC GAA GTT GAG CCT GTT GAT GCC CGC CCT GCT GCC GAC CGA GGA      430
Glu Asn Glu Val Glu Pro Val Asp Ala Arg Pro Ala Ala Asp Arg Gly
        130                 135                 140

CTG ACC ACT CGA CCA GGT TCT GGG TTG ACA AAT ATC AAG ACG GAG GAG      478
Leu Thr Thr Arg Pro Gly Ser Gly Leu Thr Asn Ile Lys Thr Glu Glu
    145                 150                 155

ATC TCT GAA GTG AAG ATG GAT GCA GAA TTC CGA CAT GAC TCA GGA TAT      526
Ile Ser Glu Val Lys Met Asp Ala Glu Phe Arg His Asp Ser Gly Tyr
160                 165                 170                 175

GAA GTT CAT CAT CAA AAA TTG GTG TTC TTT GCA GAA GAT GTG GGT TCA      574
Glu Val His His Gln Lys Leu Val Phe Phe Ala Glu Asp Val Gly Ser
                180                 185                 190

AAC AAA GGT GCA ATC ATT GGA CTC ATG GTG GGC GGT GTT GTC ATA GCG      622
Asn Lys Gly Ala Ile Ile Gly Leu Met Val Gly Gly Val Val Ile Ala
            195                 200                 205

ACA GTG ATC GTC ATC ACC TTG GTG ATG CTG AAG AAG AAA CAG TAC ACA      670
Thr Val Ile Val Ile Thr Leu Val Met Leu Lys Lys Lys Gln Tyr Thr
        210                 215                 220

TCC ATT CAT CAT GGT GTG GTG GAG GTT GAC GCC GCT GTC ACC CCA GAG      718
Ser Ile His His Gly Val Val Glu Val Asp Ala Ala Val Thr Pro Glu
    225                 230                 235

GAG CGC CAC CTG TCC AAG ATG CAG CAG AAC GGC TAC GAA AAT CCA ACC      766
Glu Arg His Leu Ser Lys Met Gln Gln Asn Gly Tyr Glu Asn Pro Thr
240                 245                 250                 255
```

-continued

```
TAC AAG TTC TTT GAG CAG ATG CAG AAC TAGACCCCCG CCACAGCAGC                    813
Tyr Lys Phe Phe Glu Gln Met Gln Asn
            260                 265

CTCTGAAGTT GGACAGCAAA ACCATTGCTT CACTACCCAT CGGTGTCCAT TTATAGAATA            873

ATGTGGGAAG AAACAAACCC GTTTTATGAT TTACTCATTA TCGCCTTTTG ACAGCTGTGC            933

TGTAACACAA GTAGATGCCT GAACTTGAAT TAATCCACAC ATCAGTAATG TATTCTATCT            993

CTCTTTACAT TTTGGTCTCT ATACTACATT ATTAATGGGT TTGTGTACT GTAAAGAATT            1053

TAGCTGTATC AAACTAGTGC ATGAATAGAT TCTCTCCTGA TTATTTATCA CATAGCCCCT           1113

TAGCCAGTTG TATATTATTC TTGTGGTTTG TGACCCAATT AAGTCCTACT TTACATATGC           1173

TTTAAGAATC GATGGGGGAT GCTTCATGTG AACGTGGGAG TTCAGCTGCT TCTCTTGCCT           1233

AAGTATTCCT TTCCTGATCA CTATGCATTT TAAAGTTAAA CATTTTTAAG TATTTCAGAT          1293

GCTTTAGAGA GATTTTTTTT CCATGACTGC ATTTACTGT ACAGATTGCT GCTTCTGCTA          1353

TATTTGTGAT ATAGGAATTA AGAGGATACA CACGTTTGTT TCTTCGTGCC TGTTTATGT           1413

GCACACATTA GGCATTGAGA CTTCAAGCTT TTCTTTTTTT GTCCACGTAT CTTTGGGTCT         1473

TTGATAAAGA AAAGAATCCC TGTTCATTGT AAGCACTTTT ACGGGGCGGG TGGGGAGGGG        1533

TGCTCTGCTG GTCTTCAATT ACCAAGAATT C                                        1564
```

( 2 ) INFORMATION FOR SEQ ID NO:5:

( i ) SEQUENCE CHARACTERISTICS:
( A ) LENGTH: 264 amino acids
( B ) TYPE: amino acid
( D ) TOPOLOGY: linear ( i i ) MOLECULE TYPE: protein ( x i ) SEQUENCE DESCRIPTION: SEQ ID NO:5:

```
His Thr Leu Lys His Phe Glu His Val Arg Met Val Asp Pro Lys Lys
 1               5                  10                  15

Ala Ala Gln Ile Arg Ser Gln Val Met Thr His Leu Arg Val Ile Tyr
             20                  25                  30

Glu Arg Met Asn Gln Ser Leu Ser Leu Leu Tyr Asn Val Pro Ala Val
         35                  40                  45

Ala Glu Glu Ile Gln Asp Glu Val Asp Glu Leu Leu Gln Lys Glu Gln
     50                  55                  60

Asn Tyr Ser Asp Asp Val Leu Ala Asn Met Ile Ser Glu Pro Arg Ile
 65                  70                  75                  80

Ser Tyr Gly Asn Asp Ala Leu Met Pro Ser Leu Thr Glu Thr Lys Thr
                 85                  90                  95

Thr Val Glu Leu Leu Pro Val Asn Gly Glu Phe Ser Leu Asp Asp Leu
            100                 105                 110

Gln Pro Trp His Ser Phe Gly Ala Asp Ser Val Pro Ala Asn Thr Glu
        115                 120                 125

Asn Glu Val Glu Pro Val Asp Ala Arg Pro Ala Ala Asp Arg Gly Leu
    130                 135                 140

Thr Thr Arg Pro Gly Ser Gly Leu Thr Asn Ile Lys Thr Glu Glu Ile
145                 150                 155                 160

Ser Glu Val Lys Met Asp Ala Glu Phe Arg His Asp Ser Gly Tyr Glu
                165                 170                 175

Val His His Gln Lys Leu Val Phe Phe Ala Glu Asp Val Gly Ser Asn
            180                 185                 190

Lys Gly Ala Ile Ile Gly Leu Met Val Gly Gly Val Val Ile Ala Thr
        195                 200                 205
```

```
Val  Ile  Val  Ile  Thr  Leu  Val  Met  Leu  Lys  Lys  Lys  Gln  Tyr  Thr  Ser
     210                 215                      220

Ile  His  His  Gly  Val  Val  Glu  Val  Asp  Ala  Ala  Val  Thr  Pro  Glu  Glu
225                      230                 235                           240

Arg  His  Leu  Ser  Lys  Met  Gln  Gln  Asn  Gly  Tyr  Glu  Asn  Pro  Thr  Tyr
                    245                      250                      255

Lys  Phe  Phe  Glu  Gln  Met  Gln  Asn
                    260
```

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( D ) TOPOLOGY: both ( x i ) SEQUENCE DESCRIPTION: SEQ ID NO:6:

```
Met  Asp  Lys  Val  Phe  Arg  Ile  Pro  Ala  Trp  Asp  Leu  Cys  Glu  Glu  Thr
1                   5                        10                       15

Leu  Leu  Leu  Trp
               20
```

( 2 ) INFORMATION FOR SEQ ID NO:7:

( i ) SEQUENCE CHARACTERISTICS:
        ( A ) LENGTH: 13 base pairs
        ( B ) TYPE: nucleic acid
        ( C ) STRANDEDNESS: both
        ( D ) TOPOLOGY: both ( x i ) SEQUENCE DESCRIPTION: SEQ ID NO:7:

AAGCTTTGCA AAG                                                                                                       13

( 2 ) INFORMATION FOR SEQ ID NO:8:

( i ) SEQUENCE CHARACTERISTICS:
        ( A ) LENGTH: 60 base pairs
        ( B ) TYPE: nucleic acid
        ( C ) STRANDEDNESS: both
        ( D ) TOPOLOGY: both ( x i ) SEQUENCE DESCRIPTION: SEQ ID NO:8:

ATGGATAAAG TTTTCCGAAT TCCAGCTTGG GATCTTTGTG AAGGAACCTT ACTTGTGTGG      60

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( D ) TOPOLOGY: both ( x i ) SEQUENCE DESCRIPTION: SEQ ID NO:9:

```
Met  Asp  Lys  Val  Leu  Asn  Arg  Glu  Glu  Phe  Gln  Leu  Gly  Ile  Phe  Val
1                   5                        10                       15

Lys  Glu  Pro  Tyr
               20
```

( 2 ) INFORMATION FOR SEQ ID NO:10:

( i ) SEQUENCE CHARACTERISTICS:
        ( A ) LENGTH: 13 base pairs
        ( B ) TYPE: nucleic acid
        ( C ) STRANDEDNESS: both
        ( D ) TOPOLOGY: both ( x i ) SEQUENCE DESCRIPTION: SEQ ID NO:10:

AACGTTTGCA AAG                                                                                      13

( 2 ) INFORMATION FOR SEQ ID NO:11:

( i ) SEQUENCE CHARACTERISTICS:
        ( A ) LENGTH: 60 base pairs
        ( B ) TYPE: nucleic acid
        ( C ) STRANDEDNESS: both
        ( D ) TOPOLOGY: both ( x i ) SEQUENCE DESCRIPTION: SEQ ID NO:11:

ATGGATAAAG TTTTAAACAG AGAGGAATTC CAGCTTGGGA TCTTTGTGAA GGAACCTTAC                                    60

( 2 ) INFORMATION FOR SEQ ID NO:12:

( i ) SEQUENCE CHARACTERISTICS:
        ( A ) LENGTH: 20 amino acids
        ( B ) TYPE: amino acid
        ( D ) TOPOLOGY: both ( x i ) SEQUENCE DESCRIPTION: SEQ ID NO:12:

Met Asp Lys Val Leu Asn Arg Glu Glu Ser Leu Gln Leu Met Asp Pro
1               5                   10                  15

Asn Ser Ser Leu
            20

( 2 ) INFORMATION FOR SEQ ID NO:13:

( i ) SEQUENCE CHARACTERISTICS:
        ( A ) LENGTH: 13 base pairs
        ( B ) TYPE: nucleic acid
        ( C ) STRANDEDNESS: both
        ( D ) TOPOLOGY: both ( x i ) SEQUENCE DESCRIPTION: SEQ ID NO:13:

AAGCTTTGCA AAG                                                                                      13

( 2 ) INFORMATION FOR SEQ ID NO:14:

( i ) SEQUENCE CHARACTERISTICS:
        ( A ) LENGTH: 60 base pairs
        ( B ) TYPE: nucleic acid
        ( C ) STRANDEDNESS: both
        ( D ) TOPOLOGY: both ( x i ) SEQUENCE DESCRIPTION: SEQ ID NO:14:

ATGGATAAAG TTTTAAACAG AGAGGAATCT TTGCAGCTAA TGGACCCGAA TTCCAGCTTG                                    60

( 2 ) INFORMATION FOR SEQ ID NO:15:

( i ) SEQUENCE CHARACTERISTICS:
        ( A ) LENGTH: 36 base pairs
        ( B ) TYPE: nucleic acid
        ( C ) STRANDEDNESS: both
        ( D ) TOPOLOGY: both ( x i ) SEQUENCE DESCRIPTION: SEQ ID NO:15:

ATGGATAAAG TTTTCCGAAT TGCCGCGGCA ATTCCA                                                              36

( 2 ) INFORMATION FOR SEQ ID NO:16:

( i ) SEQUENCE CHARACTERISTICS:
        ( A ) LENGTH: 39 base pairs
        ( B ) TYPE: nucleic acid
        ( C ) STRANDEDNESS: both
        ( D ) TOPOLOGY: both ( x i ) SEQUENCE DESCRIPTION: SEQ ID NO:16:

ATGGATAAAG TTTTAAACAG AGAGGAATTG CCGCGGCAA 39

( 2 ) INFORMATION FOR SEQ ID NO:17:

( i ) SEQUENCE CHARACTERISTICS:
( A ) LENGTH: 39 base pairs
( B ) TYPE: nucleic acid
( C ) STRANDEDNESS: both
( D ) TOPOLOGY: both ( x i ) SEQUENCE DESCRIPTION: SEQ ID NO:17:

ATGGATAAAG TTTTAAACAG AGAGGAATCT TTGCAGCTA 39

( 2 ) INFORMATION FOR SEQ ID NO:18:

( i ) SEQUENCE CHARACTERISTICS:
( A ) LENGTH: 30 base pairs
( B ) TYPE: nucleic acid
( C ) STRANDEDNESS: both
( D ) TOPOLOGY: both ( x i ) SEQUENCE DESCRIPTION: SEQ ID NO:18:

ATGGACCCGA ATTGCCGCGG CAATTCCAGC 30